(12) United States Patent
Baker et al.

(10) Patent No.: US 10,187,736 B2
(45) Date of Patent: Jan. 22, 2019

(54) SYSTEMS AND METHODS FOR TRACKING AND PRESENTING TINNITUS THERAPY DATA

(71) Applicant: Otoharmonics Corporation, Portland, OR (US)

(72) Inventors: Michael Baker, Portland, OR (US); Brenda Edin, Portland, OR (US); Daniel Drexler, Montevideo (UY); Marisa Pedemonte Benvenuto, Montevideo (UY); Dario Geisinger Yasky, Givat Shmuel (IL); Andres Bianco de Olea, Lomas de Solymar (UY)

(73) Assignee: Otoharmonics Coporation, Portland, OR (US)

( * ) Notice: Subject to any disclaimer, the term of this patent is extended or adjusted under 35 U.S.C. 154(b) by 0 days.

(21) Appl. No.: 15/971,401

(22) Filed: May 4, 2018

(65) Prior Publication Data

US 2018/0255410 A1 Sep. 6, 2018

Related U.S. Application Data

(63) Continuation of application No. 15/057,589, filed on Mar. 1, 2016, now Pat. No. 9,992,590, which is a
(Continued)

(51) Int. Cl.
*H04R 25/00* (2006.01)
*A61B 5/00* (2006.01)
(Continued)

(52) U.S. Cl.
CPC ............. *H04R 25/75* (2013.01); *A61B 5/128* (2013.01); *A61B 5/4836* (2013.01);
(Continued)

(58) Field of Classification Search
CPC ...... H03G 3/3089; H03G 3/3005; H03G 3/32; H03G 9/025; H03G 9/005; H03G 3/001; H03G 5/165; H03G 3/10
(Continued)

(56) References Cited

U.S. PATENT DOCUMENTS

| 5,403,262 A | 4/1995 | Gooch |
| 6,682,472 B1 | 1/2004 | Davis |

(Continued)

OTHER PUBLICATIONS

"About HushTinnitus," HushTinnitus Website, Available Online at http://www.hushtinnitus.com/about, Available as Early as Nov. 16, 2014, 3 pages.
(Continued)

*Primary Examiner* — Mark Blouin
(74) *Attorney, Agent, or Firm* — McCoy Russell LLP

(57) ABSTRACT

The treatment of tinnitus may include a tinnitus therapy including generating a tinnitus therapy sound that is similar to a patient's perceived tinnitus sound. In one example, a method for tinnitus therapy may include tracking a tinnitus therapy over a duration, the tinnitus therapy including a tinnitus therapy sound matching a patient's perceived tinnitus played over the duration and presenting each of a volume evolution of the tinnitus therapy sound and usage data of the tinnitus therapy over the duration.

20 Claims, 21 Drawing Sheets

Related U.S. Application Data continuation of application No. 14/317,374, filed on Jun. 27, 2014, now Pat. No. 9,301,714.

(60) Provisional application No. 61/841,221, filed on Jun. 28, 2013, provisional application No. 61/841,254, filed on Jun. 28, 2013.

(51) Int. Cl.
*G16H 15/00* (2018.01)
*H03G 3/00* (2006.01)
*A61B 5/12* (2006.01)

(52) U.S. Cl.
CPC .......... *A61B 5/4848* (2013.01); *G16H 15/00* (2018.01); *H03G 3/00* (2013.01); *H04R 25/50* (2013.01); *A61B 5/0022* (2013.01); *A61B 5/4842* (2013.01)

(58) Field of Classification Search
USPC ...................................................... 381/104
See application file for complete search history.

(56) References Cited

U.S. PATENT DOCUMENTS

| | | |
|---|---|---|
| 7,081,085 B2 | 7/2006 | Viirre et al. |
| 7,347,827 B2 | 3/2008 | Choy |
| 7,572,234 B2 | 8/2009 | Viirre et al. |
| 7,850,596 B2 | 12/2010 | Davis et al. |
| 7,981,047 B2 | 7/2011 | Viirre et al. |
| 8,043,203 B2 | 10/2011 | Park et al. |
| 8,098,859 B2 | 1/2012 | Zeng et al. |
| 8,185,383 B2 | 5/2012 | Zeng et al. |
| 8,273,034 B2 | 9/2012 | Fogel et al. |
| 8,306,248 B2 | 11/2012 | DiGiovanni et al. |
| 8,357,102 B2 | 1/2013 | Zeng et al. |
| 8,608,638 B2 | 12/2013 | McGuire |
| 8,666,501 B2 | 3/2014 | Kilgard et al. |
| 8,870,786 B2 | 10/2014 | Henry et al. |
| 2007/0093733 A1 | 4/2007 | Choy |
| 2007/0203535 A1 | 8/2007 | Zeng et al. |
| 2009/0018466 A1* | 1/2009 | Materna ................ A61B 5/121 600/559 |
| 2009/0099474 A1* | 4/2009 | Pineda ................... A61B 5/121 600/545 |
| 2009/0124850 A1 | 5/2009 | Moore et al. |
| 2009/0307590 A1 | 12/2009 | Frater et al. |
| 2010/0208631 A1 | 8/2010 | Zhang et al. |
| 2011/0054243 A1 | 3/2011 | Davis et al. |
| 2011/0071340 A1 | 3/2011 | McGuire |
| 2011/0245235 A1 | 10/2011 | Hanley et al. |
| 2012/0046713 A1 | 2/2012 | Hannemann et al. |
| 2012/0283593 A1 | 11/2012 | Searchfield et al. |
| 2013/0039517 A1 | 2/2013 | Nielsen et al. |
| 2013/0204170 A1 | 8/2013 | Zeng et al. |
| 2013/0253258 A1 | 9/2013 | Davis et al. |

OTHER PUBLICATIONS

European Patent Office, Extended European Search Report Issued in Application No. 14818503.6, dated Jan. 26, 2017, Germany, 7 pages.

\* cited by examiner

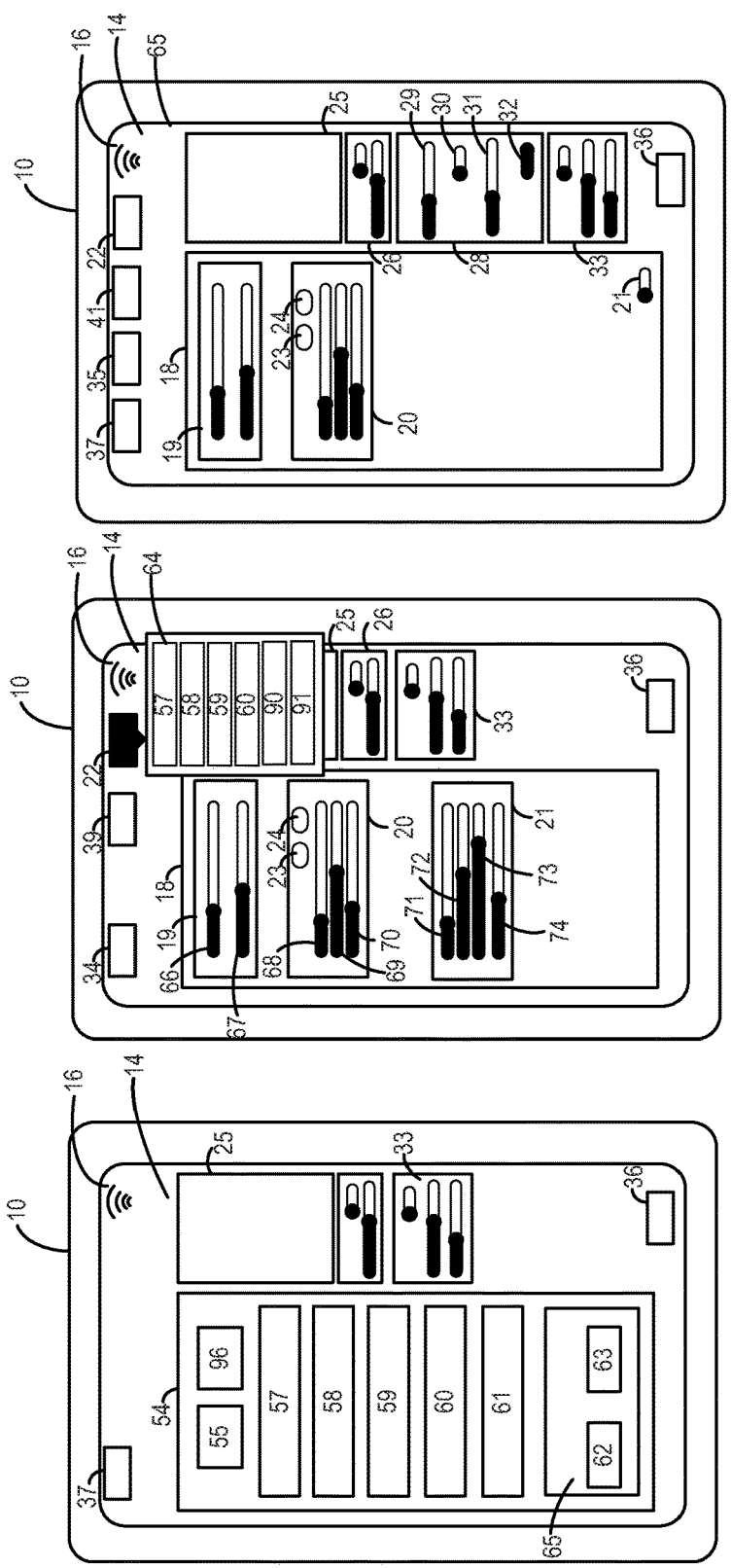

1502 — Evolution Report — 1400 — Patient #2 - ID:Test Patient 3

Therapy 1 — 2012-10-14

1504 →
| | | Left | Right |
|---|---|---|---|
| Pure Tone | 2205 Hz | 78 dB | 72 dB |
| | Total | 78 dB | 72 dB |

1506 →
Max. allowed stimulation time: 7 h  Allow Volume Change: YES
Allow HTS: NO  HTS Timeout: -

Therapy 2 — 2012-10-07

| | | Left | Right |
|---|---|---|---|
| Pure Tone | 2205 Hz | 78 dB | 72 dB |
| | Total | 78 dB | 72 dB |

Max. allowed stimulation time: 4 h  Allow Volume Change: YES
Allow HTS: NO  HTS Timeout: -

Therapy 3 — 2012-09-30

| | | Left | Right |
|---|---|---|---|
| Pure Tone | 2205 Hz | 78 dB | 72 dB |
| | Total | 78 dB | 72 dB |

Max. allowed stimulation time: 0 h  Allow Volume Change: YES
Allow HTS: NO  HTS Timeout: -

Therapy 4 — 2012-09-23

1508 →
| | | Left | Right |
|---|---|---|---|
| Pure Tone | 2205 Hz | 78 dB | 72 dB |
| | Total | 78 dB | 72 dB |

Max. allowed stimulation time: 0 h  Allow Volume Change: YES
Allow HTS: NO  HTS Timeout: -

Therapy 5 — 2012-09-16

| | | Left | Right |
|---|---|---|---|
| Pure Tone | 2205 Hz | 80 dB | 76 dB |
| | Total | 80 dB | 76 dB |

Max. allowed stimulation time: 3 h  Allow Volume Change: YES
Allow HTS: NO  HTS Timeout: -

Therapy 6 — 2012-09-09

| | | Left | Right |
|---|---|---|---|
| Pure Tone | 2205 Hz | 80 dB | 76 dB |

Page: 2

FIG. 15

SYSTEMS AND METHODS FOR TRACKING AND PRESENTING TINNITUS THERAPY DATA

CROSS REFERENCE TO RELATED APPLICATIONS

The present application is a continuation of U.S. patent application Ser. No. 15/057,589, entitled "SYSTEMS AND METHODS FOR TRACKING AND PRESENTING TINNITUS THERAPY DATA" filed on Mar. 1, 2016. U.S. patent application Ser. No. 15/057,589 is a continuation of U.S. patent application Ser. No. 14/317,374, entitled "SYSTEMS AND METHODS FOR TRACKING AND PRESENTING TINNITUS THERAPY DATA," filed on Jun. 27, 2014, now U.S. Pat. No. 9,301,714. U.S. patent application Ser. No. 14/317,374 claims priority to U.S. Provisional Application No. 61/841,221 filed on Jun. 28, 2013. U.S. patent application Ser. No. 14/317,374 claims further priority to U.S. Provisional Application No. 61/841,254 filed on Jun. 28, 2013. The entire contents of each of the above-listed applications are hereby incorporated by reference for all purposes.

BACKGROUND AND SUMMARY

Tinnitus is the sensation of hearing sounds when there are no external sounds present and can be loud enough to attenuate the perception of outside sounds. Tinnitus may be caused by inner ear cell damage resulting from injury, age related hearing loss, and exposure to loud noises. The tinnitus sound perceived by the affected patient may be heard in one or both ears and also may include ringing, buzzing, clicking, and/or hissing.

Some methods of tinnitus treatment and/or therapy include producing a sound in order to mask the tinnitus of the patient. One example is shown by U.S. Pat. No. 7,850,596 where the masking treatment involves a pre-determined algorithm that modifies a sound similar to a patient's tinnitus sound.

However, the inventors herein have recognized issues with such approaches. For example, the modified sound used in the treatment is generated using a masking algorithm that only partially modifies the spectral qualities of the tinnitus sound. As such, the modified tinnitus sound includes the tinnitus sound of broad band noise only. Thus, an individual patient's tinnitus sound may not be completely masked by the modified tinnitus sound. Additionally, such systems of masking a patient's tinnitus sound may not offer the ability to adjust the sound based on the evolution of a patient's tinnitus over time.

In one example, a method for tinnitus therapy may include tracking a tinnitus therapy over a duration, the tinnitus therapy including a tinnitus therapy sound matching a patient's perceived tinnitus played over the duration and presenting each of a volume evolution of the tinnitus therapy sound and usage data of the tinnitus therapy over the duration. In this way, changes to a patient's tinnitus therapy may be tracked over a period of treatment.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 1A-1E show schematic diagrams of example devices for a tinnitus therapy including a healthcare professional's device and a patient's device.

FIGS. 14-15 show schematics of a report generated from tracked data of a patient's tinnitus therapy.

DETAILED DESCRIPTION

Methods and systems are provided for tinnitus therapy generation, tracking, and reviewing. In another example, the methods and systems may be adapted for other audio therapies or neurological disorders and treatments. In one embodiment, tinnitus therapy for the treatment of tinnitus may include therapy sessions and tracking of the therapy sessions generated and carried out on a healthcare professional's device and a patient's device, such as the healthcare professional's device and patient's device shown in FIGS. 1A-1E. FIGS. 2, 3A-3D, and 4 show methods for generating a tinnitus therapy (e.g., therapy sessions) for an individual patient's perceived tinnitus using the healthcare professional's device. The tinnitus therapy may include a tinnitus therapy sound generated by user inputs via the healthcare professional's device. The tinnitus therapy sound may be based on and include one or more types of sounds. For example, different types of sounds such as white noise, pink noise, pure tone, broad band noise, and cricket noise may be included in the tinnitus therapy sound. Specific tinnitus therapy sounds, or sound templates, may be pre-determined and include a white noise sound, a pink noise sound, a pure tone sound, a broad band noise sound, a cricket noise sound, an amplitude modulated sine wave, and/or a combine tone sound. A user may be presented with one or more of the above tinnitus therapy sound templates via the healthcare professional's device. Using a plurality of user interfaces of the healthcare professional's device, a user may select and modify one or more tinnitus therapy sound templates in order to generate a tinnitus therapy sound similar to the user's or patient's perceived tinnitus. However, the modifications do not include adding further amplitude of frequency modulation to the templates. In one example, a user may include a medical provider such as a physician, nurse, technician, audiologist, or other medical personnel. In another example, the user may include a patient.

Figure 5A:
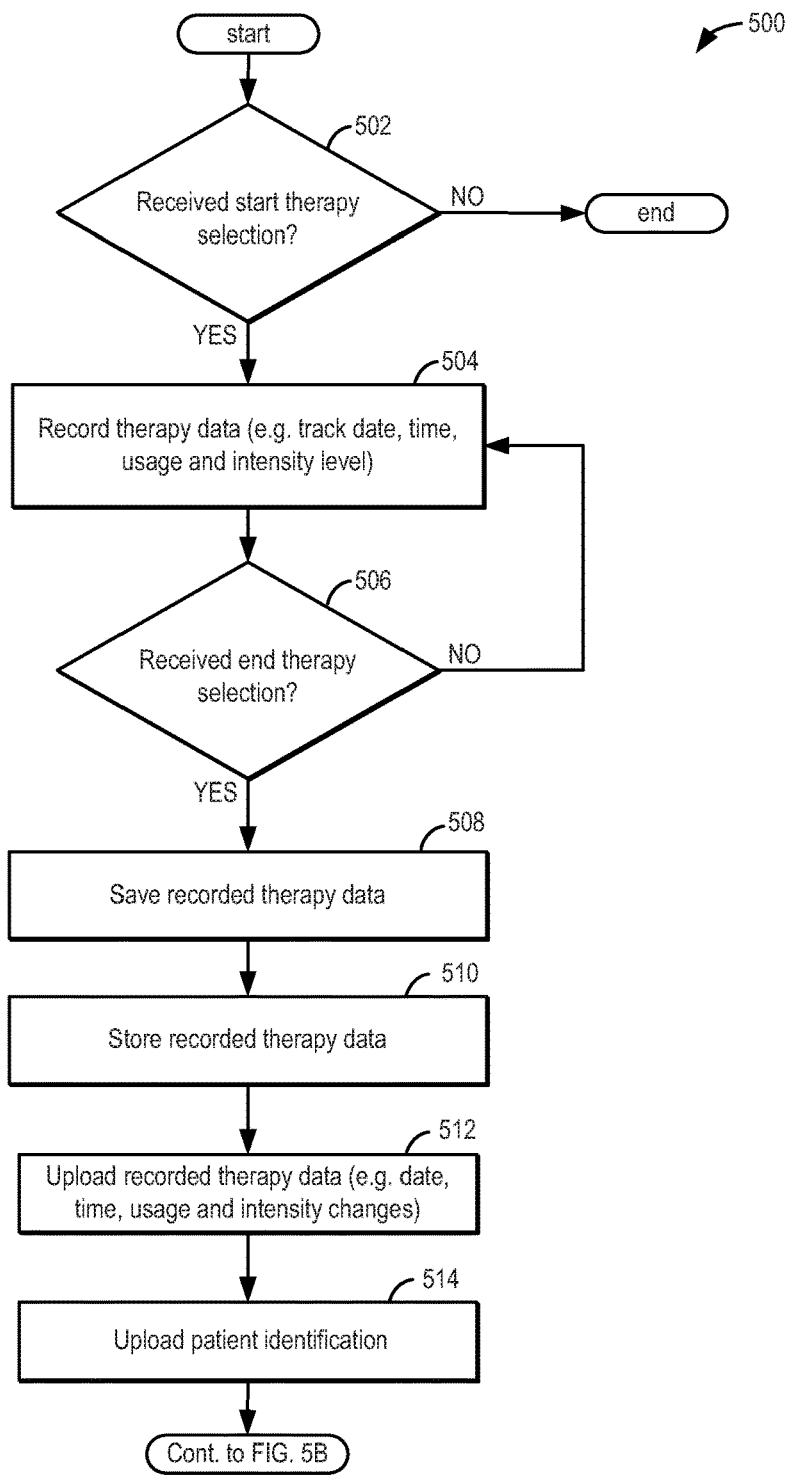
FIGS. 5A-5B show an example method for tracking patient data.
Figure 5B:
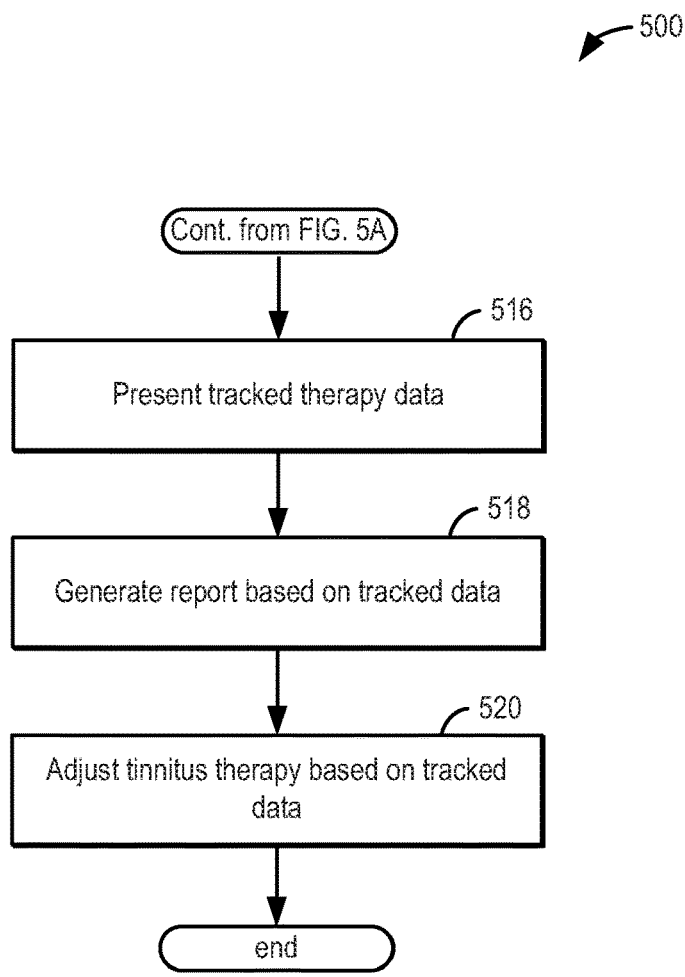

Additionally, the tinnitus therapy may be tracked over time using the patient's device, as shown at FIGS. 5A-5B. The tracked data may then be presented to a user, used to generate a report, and/or used to adjust the tinnitus therapy, as shown at FIGS. 6-15.

Thus, the healthcare professional's tinnitus therapy device may include a plurality of displays including a user interface for the input of patient data, tracking patient data, selecting tinnitus therapy sound templates, adjusting a tinnitus therapy sound template, and generating a tinnitus therapy sound. Various input buttons or controls on the one or more user interfaces of the healthcare professional's device may be adjusted in order to modify the tinnitus therapy sound. For example, by adjusting various input buttons, sound parameters of the tinnitus therapy sound templates and/or tinnitus therapy sound may be altered.

Additionally, a patient's device may include a plurality of displays including user interfaces for performing the tinnitus therapy and adjusting the volume of the tinnitus therapy. A patient's device may be used to perform the tinnitus therapy over a set duration of time. Further, a patient's device may include a customized visual representation so an individual patient may be able to view their progress of the tinnitus therapy. A patient's device may also track adjustments made to the tinnitus therapy sound including volume adjustments. Additionally, the device may also track user data including hearing threshold data from an audiogram, patient information, and/or adjustments to the customized visual representation.

Figure 1A:
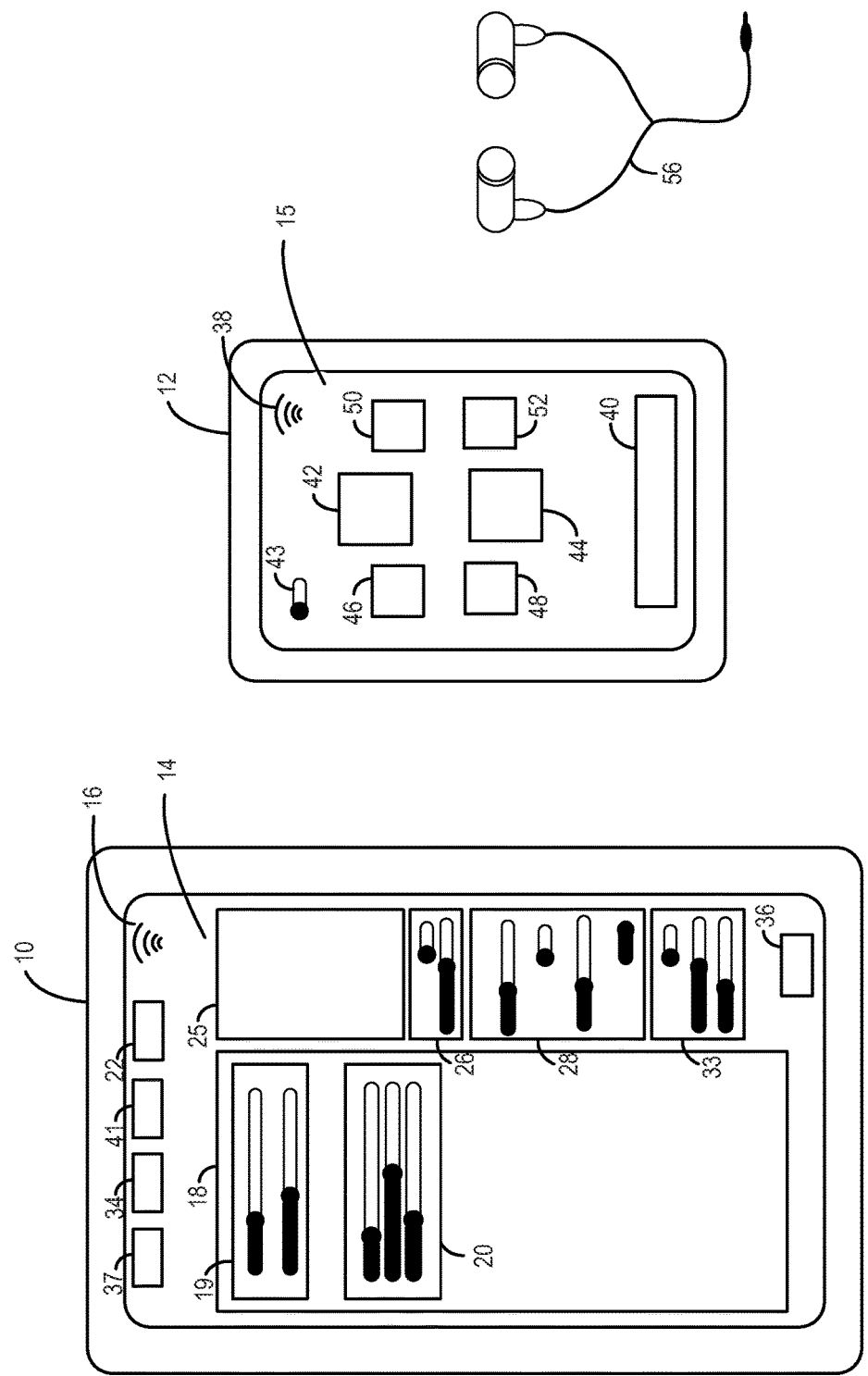

Referring to FIG. 1A, the figure shows a schematic diagram of example devices for a tinnitus therapy including healthcare professional's device 10 and patient's device 12. Healthcare professional's device 10 may be used and/or operated by a medical provider including, but not limited to, physicians, audiologists, nurses, and/or technicians. In another example, healthcare professional's device 10 may be used and/or operated by a patient. Thus, the user of the healthcare professional's device may be one or more of a patient or a medical provider. Further, the user of the patient's device may be the patient.

Healthcare professional's device 10 and patient's device 12 are physical, non-transitory devices configured to hold data and/or instructions executable by a logic subsystem. The logic subsystem may include individual components that are distributed throughout two or more devices, which may be remotely located and/or configured for coordinated processing. One or more aspects of the logic subsystem may be virtualized and executed by remotely accessible networked computing devices. Healthcare professional's device 10 and patient's device 12 may be configured to execute one or more instructions related to a tinnitus therapy. In addition, healthcare professional's device 10 and patient's device 12 may also include a user interface (e.g., display screens 14 and 15) for displaying information to the user and receiving digital information from the user, such as patient information and adjustments to the tinnitus therapy. In one example, the display screen(s) may be a touch screen. Information received from the user may be in various digital forms that represent a user's inputs. For example, the user may enter text, select, and/or move slide bars or other adjustable input buttons. In the example of the display screen being a touch screen, the user may adjust the input buttons through the touch screen. In another example, if the display screen is not a touch screen, the user may adjust the input buttons through a secondary device such as a computer mouse and/or keyboard. Further, healthcare professional's device 10 and patient's device 12 may generate tinnitus therapy sound templates and tinnitus therapy sounds to transmit the automatically generated electronic tinnitus therapy to the user. In one example, healthcare professional's device 10 and patient's device 12 may interact via a wired or wireless network which may allow for bidirectional communication between the devices. In another example, a patient's device 12 may track and/or record tinnitus therapy data, including metadata, that may be transmitted to the healthcare professional's device 10. In another example, recorded and/or stored therapy data may be written in an HTML5 format such that the transferred data, via a remote portal, may be received on a secured webpage.

Continuing with FIG. 1A, display screen 14 of healthcare professional's device 10 may include a plurality of input buttons for selecting sound parameters, such as frequency, intensity, harmonics, Q factor, reverberation, and/or white noise edge enhancement. Further, display screen 14 may display different combinations of input buttons and graphics based on a selected user interface. Additional details and examples of sample user interfaces are presented below with reference to FIGS. 1B-1E.

In the example shown in FIG. 1A, display screen 14 includes controls for generating a tinnitus therapy sound. The tinnitus therapy sound generated with the methods described below may also be referred to herein as a tinnitus sound match or a tinnitus therapy sound match. The controls used for generating the tinnitus sound match include tinnitus sound match input button 37, generating a tinnitus therapy via therapy input button 34, copying a tinnitus sound match via copy tinnitus sound match input button 41, and adding a template to the tinnitus therapy via add template input button 22 (see also FIGS. 1B-1D). The tinnitus therapy sound may be generated based on adjustments to pre-defined tinnitus therapy templates, the pre-defined tinnitus therapy templates including a tinnitus therapy sound or combination of sounds (e.g., cricket noise, broad band noise, pure tone and broad band noise, etc.) within certain frequency and intensity ranges. The pre-defined tinnitus therapy templates may be modified by patient-specific hearing threshold data such that the tinnitus therapy sound template includes a tinnitus therapy sound audible to the patient.

In one example, once a tinnitus therapy sound template is selected, specific tinnitus therapy sound template displays may be displayed in tinnitus therapy sound display 18 (e.g., sound list) which may include a first tinnitus therapy sound template display 19 and a second tinnitus therapy sound template display 20 in order to generate a specific tinnitus therapy, or tinnitus therapy sound (see also FIG. 1C). Each tinnitus therapy sound template display may include a specific tinnitus therapy sound template (e.g., cricket noise, broad band noise, etc.), along with various input buttons to adjust sound parameters of the tinnitus therapy sound template. In one example, a first tinnitus therapy sound template display 19 and a second tinnitus therapy sound template display 20 may include a cricket noise sound template, a white noise sound template, a pure tone sound template, and/or a broad band noise sound template. In addition, a tinnitus therapy sound template display may include a set of controls and/or adjustments for modifying the sound characteristics of the tinnitus therapy sound template. The controls and/or adjustments may include a volume adjustment (e.g. intensity adjustment), a frequency adjustment (e.g., pitch adjustment), a timbre adjustment, a Q factor adjustment, a vibrato adjustment, a reverberation adjustment, and/or a white noise edge enhancement adjustment. As such, the controls and/or adjustments of a template may include an input button and/or slide bar input.

Display screen 14 may also include a session notes window 25 that includes a space to input notes about a tinnitus therapy. Notes written in the session notes window 25 may be displayed as part of the tinnitus therapy. Further, a sound monitor 26 adjusts the volume of the healthcare professional's device. In one example, sound monitor 26 generates a sound output in order for the tinnitus therapy sound match to be monitored via an external speaker of the healthcare professional's device 10 (not shown).

Display screen 14 may include a therapy parameter window 28. In one example, therapy parameter window 28 may also include a help-to-sleep option, a changing volume option, and a maximum duration option. The additional features of the therapy parameter window 28 are described further below with regard to FIG. 1D. Further, a sound option 33 enables the physician to adjust the volume of the generated tinnitus sound match on a patient's device 12. For example, when sound option 33 is activated on a healthcare professional's device, a user may be able to adjust the tinnitus therapy volume of the patient's device via the healthcare professional's device.

In order to complete the tinnitus therapy, when selected, an end session input button 36, or similar input button, saves the tinnitus therapy to healthcare professional's device 10. A wireless input 16 sends the tinnitus therapy to a patient's device 12. In one example, once the therapy is completed and the session ends, a patient's device 12 is connected to healthcare professional's device 10 and the tinnitus therapy is loaded onto patient's device 12. In another example, after completing the tinnitus therapy on the healthcare professional's device 10, the completed tinnitus therapy (or tinnitus therapy sound) may be e-mailed over a secure network which may then be accessed via an internet connection on the patient's device 12. In yet another example, the competed tinnitus therapy sound may be transferred between the healthcare professional's device 10 and the patient's device 12 by bidirectional communication via a wired connection or a portable storage device.

Patient's device 12 may include a set of customized earphones 56. In one example, the earphones 56 are made from medical grade silicon and are custom molded and handcrafted to a patient's ears. Further, earphones 56 may be used while generating a tinnitus therapy via a healthcare professional's device as well as during the tinnitus therapy via the patient's device. In another example, another type of earphones or listening device may be used during generating the tinnitus therapy and during listening to the generated tinnitus therapy (e.g., tinnitus sound match). In some examples, a different set of earphones may be used while generating the tinnitus therapy via the healthcare professional's device 10 than when listening to the generated tinnitus therapy via the patient's device 12.

In another example, patient's device 12 can be used for either day or night treatment. If a night treatment is selected, a user interface may include a display screen 15 including a help-to-sleep input 43, and a wireless input 38. When selected, the help-to-sleep option plays a pre-determined sound (e.g., music). The pre-determined sound is separate from the tinnitus therapy, the tinnitus therapy including the tinnitus therapy sound match. Further, the pre-determined sound may be played for a pre-determined amount of time (e.g., 1-60 minutes).

When the allow changing volume option from the therapy parameter window 28 on healthcare professional's device 10 is selected as part of the tinnitus therapy, the patient's device 12 includes a user interface that may have a volume adjustment inputs 42 and 44 on display screen 15. In one example, display screen 15 may have volume adjustment inputs 46 and 48 for the left ear and volume adjustment inputs 50 and 52 for the right ear. Volume adjustment inputs 46, 48, 50, and 52 may be adjusted independently from volume adjustment inputs 42 and 44. In another example, the volume can be adjusted following the selection of the help-to-sleep option using volume adjustment inputs 46, 48, 50, and 52, as well as volume adjustment inputs 42 and 44. In another example, volume adjustment input 42 may increase the volume of the tinnitus sound match where as volume adjustment 44 may decrease the volume of the tinnitus sound match when selected. Further, volume adjustment inputs 46 and 50 may increase the volume of the left ear and right ear inputs, respectively. Conversely, volume adjustment inputs 48 and 52 may decrease the volume of the left ear and right ear inputs, respectively.

In order to start a tinnitus therapy, a user interface may include a display screen 15 including a start therapy input button 40. In this example, the pre-defined tinnitus therapy from healthcare professional's device 10 will begin once the start therapy input 40 is selected. The tinnitus therapy will play for a set duration of time based on the input from the therapy parameter window 28 on healthcare professional's device 10. For example, the tinnitus sound match created for the tinnitus therapy may play repeatedly without breaks for the designated duration of time. The start therapy input 40 may also be selected during a tinnitus therapy session in order to pause the therapy.

FIGS. 1B-1D show schematic diagrams of a healthcare professional's device including example user interfaces. In particular, FIG. 1B shows a sample tinnitus sound template selection display, FIG. 1C shows a sample tinnitus sound display (e.g., tinnitus sound match display), and FIG. 1D shows a sample therapy display, as explained above and shown at FIG. 1A. In one example, generating a tinnitus therapy involves selecting the appropriate tinnitus therapy sound template, generating a tinnitus therapy sound based on adjustments of the tinnitus therapy sound template, and choosing specific therapy parameters.

Now referring to FIG. 1B, a healthcare professional's device 10 may include a user interface that may include a plurality of tinnitus therapy sound template selections or displays which may be used to generate a tinnitus therapy sound. In this example, display screen 14 includes a tinnitus therapy sound template selection display 54. A tinnitus therapy sound template selection display 54 includes audiogram inputs including a hearing level input 55 and a frequency input 96. In one example, when a hearing level input 55 and a frequency input 96 are selected, a user interface may prompt a user to input hearing threshold data (e.g. intensity and frequency thresholds). In another example, tinnitus therapy sound template selection display 54 may include a hearing test including a user generated audiogram. Specifically, a user interface may prompt a user to perform a hearing test. Upon completion of the hearing test, an audiogram may be generated based on user inputs. Based on the generated audiogram, a user interface may prompt a user to input the hearing threshold data into hearing level input 55 and frequency input 96. In another example, hearing threshold data from the generated audiogram may automatically fill into the hearing level input 55 and/or the frequency input 96 without further input from the user. In addition, tinnitus therapy sound template selection display 54 includes controls for selecting a plurality of tinnitus therapy sound templates. The tinnitus therapy sound template controls may include cricket noise sound template 57, white noise sound template 58, pure tone sound template 59, broad band noise sound template 60, a combination pure tone and broad band noise sound template 61, pink noise sound template 90, and amplitude modulated sine wave template 91. In an alternate example, the tinnitus therapy sound template controls (e.g., sound type options) may include cricket noise sound template 57, white noise sound template 58, pure tone sound template 59, broad band noise sound template 60, pink noise sound template 90, and amplitude (or frequency) modulated sine wave template 91.

In one example, when a tinnitus therapy sound template is selected (e.g., one of sound templates 57-61 and 90-91), a pre-defined tinnitus therapy sound template may be played and heard from an external speaker (not shown). For example, a pre-defined tinnitus therapy sound template may be generated and/or modified based on the hearing threshold data of an individual patient's audiogram. Following selection of a tinnitus therapy sound template, a user interface may prompt a user to confirm the tinnitus therapy sound template selection via display 65. Display 65 includes verification inputs 62 and 63, that when selected, confirm if the tinnitus therapy sound template selected is the correct template to be used for the tinnitus therapy. For example, if cricket noise sound template 57 is selected and the cricket noise played is similar to the patient's perceived tinnitus, then input 62 is selected. Conversely, if the cricket noise sound template played is not similar to the patient's perceived tinnitus, then input 63 is selected. Display screen 14 also includes a tinnitus therapy sound match input button 37. When the tinnitus therapy sound match input button 37 is selected, a user interface may include a tinnitus therapy sound display, as described further below with regard to FIG. 1C.

Now referring to FIG. 1C, in this example, display screen 14 of healthcare professional's device 10 includes a user interface including a tinnitus sound display (e.g., tinnitus sound match refinement display). As such, display screen 14 may include a tinnitus therapy sound display 18 including a first tinnitus therapy sound template display 19 and a second tinnitus therapy sound template display 20. In one example, the tinnitus therapy sound template or combination of tinnitus therapy sound templates displayed on the tinnitus therapy sound display 18 may be those selected from the tinnitus therapy sound template selection display 54. As such, tinnitus therapy sound display 18 may include one or more selected tinnitus therapy sound template displays including a cricket noise sound template display, a white noise sound template display, a pink noise sound template display, a pure tone sound template display, a broad band noise template display, an amplitude modulated sine wave template, and/or a combination pure tone and broad band noise sound template display. In this example, first tinnitus therapy sound template 19 may be a white noise sound template display and second tinnitus therapy sound template 20 may be a pure tone sound template display. In other examples, tinnitus therapy sound display 18 may include other tinnitus therapy sound template display combinations such as a white noise sound template display combined with a broad band noise sound template display. In another example, a pure tone sound template display may be combined with a broad band noise sound template display.

In one example, tinnitus therapy sound template display 19 includes volume adjustment inputs 66 and 67 for both left and right ears, respectively (e.g. a white noise sound template). In another example, tinnitus therapy sound template display 20 includes volume adjustment inputs 68 and 69 for both left and right ears, respectively, an adjustment input for frequency 70, and octave adjustment inputs 23 and 24 (e.g., a pure tone sound template). In another example, tinnitus therapy sound display 18 may include tinnitus therapy sound template display 21 for a broad band noise sound template which may include volume adjustment inputs 71 and 72 for both left and right ears, an adjustment for frequency input 73, and an adjustment for Q-factor input 74. Further, a cricket noise sound template display may include adjustment inputs for both left and right ears and an adjustment input for frequency. In another example, tinnitus therapy sound template displays may include a vibrato adjustment, reverberation adjustment, and/or a white noise edge enhancement adjustment.

After adjusting the tinnitus therapy sound templates via the tinnitus therapy sound template displays, additional tinnitus therapy sound template displays may be added to tinnitus therapy sound display 18. By selecting the add template input button 22, a user interface may prompt a user to select an additional tinnitus therapy sound template display from tinnitus therapy sound template display 64. Tinnitus therapy sound template display 64 includes a plurality of tinnitus therapy sound templates including cricket noise sound template 57, white noise sound template 58, pure tone sound template 59, broad band noise sound template 60, a combination pure tone and broad band noise sound template, pink noise sound template 90, and amplitude modulated sine wave template 91. In alternate embodiments, the tinnitus therapy sound template display 64 may include a different combination of cricket noise sound template 57, white noise sound template 58, pure tone sound template 59, broad band noise sound template 60, a combination pure tone and broad band noise sound template, pink noise sound template 90, and amplitude modulated sine wave template 91. For example, the tinnitus therapy sound template display 64 may include cricket noise sound template 57, white noise sound template 58, pure tone sound template 59, broad band noise sound template 60, and pink noise sound template 90. In yet another example, the tinnitus therapy sound template display 64 may include white noise sound template 58, pure tone sound template 59, and a combined tone sound template, the combined tone tinnitus sound template including the combination pure tone and broad band noise sound template. Once a tinnitus therapy sound template is selected, the tinnitus therapy sound template display may be displayed in tinnitus therapy sound display 18 where the template(s) may then be adjusted. As such, the add template input button 22 enables a user to add additional tinnitus therapy sound template displays. For example, following selection of the add template input, two or more tinnitus therapy sound template displays may be displayed in tinnitus therapy sound display. Specifically, a user may select add template input button 22 in order to add a second tinnitus therapy sound template following adjustment of a first tinnitus therapy sound template. For example, a first tinnitus therapy sound template may be a white noise sound template and a second tinnitus therapy sound template may be a pure tone sound template. As such, a white noise template may be adjusted prior to addition of the pure tone sound template. Following the adjustment of the white noise sound template, a pure tone sound template may be adjusted. In an additional example, a first tinnitus therapy sound template and a second tinnitus therapy sound template may be adjusted simultaneously. In this way, a pure tone template may be added to the tinnitus therapy display prior to a white noise sound template adjustment and both the white noise and pure tone sound templates may be adjusted together. Adjusting the template may include, for example, adjusting frequency, intensity, timbre, vibrato, Q factor, reverberation, and/or white noise edge enhancement. Following the adjustment of the first and second tinnitus therapy sound templates, the tinnitus therapy sound templates may be combined to create a tinnitus therapy sound.

Display screen 14 of healthcare professional's device 10 including the tinnitus therapy sound display 18, may include controls for selecting a therapy display via therapy input button 34 and loading a previously generated and saved tinnitus sound via load match input button 39. Following the conclusion of the tinnitus therapy sound process, a therapy input button 34 may be selected and a user interface may include a tinnitus therapy including therapy parameter window 28 as described further below with regard to FIG. 1D. Further, before adjusting the tinnitus therapy sound templates displayed in tinnitus therapy sound display 18, a load tinnitus sound match input button may be selected and a user interface may include the previously adjusted tinnitus sound template in the tinnitus therapy sound display 18.

Referring now to FIG. 1D, in this example, display screen 14 of healthcare professional's device 10 shows an example tinnitus therapy screen. Display screen 14 includes a therapy parameter window 28. In one example, therapy parameter window 28 includes the help-to-sleep option 30, allow changing volume option 32, and maximum duration input 29. The help-to-sleep option delays the start of the tinnitus therapy for use during night therapy. The help-to-sleep option includes a timeout option 31 that adjusts the time in which the help-to-sleep feature is active (e.g., 1-60 minutes). The allow changing volume option 32 enables modification of the tinnitus sound volume during therapy. However, if this option is turned off, the volume will stay as established by the physician (or other user) during the generation of the tinnitus therapy. The therapy parameter window 28 may also include a maximum duration input 29 that sets a maximum time duration for playing the tinnitus therapy (e.g., 1-8 hours).

Further, display screen 14 may include controls for generating a tinnitus therapy sound match via tinnitus sound match input button 37, loading a previously generated tinnitus therapy via a tinnitus therapy input button 35, copying a tinnitus therapy sound match via copy tinnitus sound match input button 41, and adding a template via add template input button 22. For example, before adjusting the therapy parameters, tinnitus therapy input button 35 may be selected and a graphical user interface will display a previously adjusted tinnitus therapy in therapy parameter window 28. The therapy input button may be selected if no modifications to the therapy parameters are required. Following the selection of the therapy parameters for the tinnitus therapy, a tinnitus match input button 37 may be selected and a user interface may include a tinnitus match display including previously selected tinnitus sound templates. A match input button 37 may be selected, for example, if further modifications to the tinnitus therapy sound templates need to be made before finalizing the tinnitus therapy.

Figure 1E:
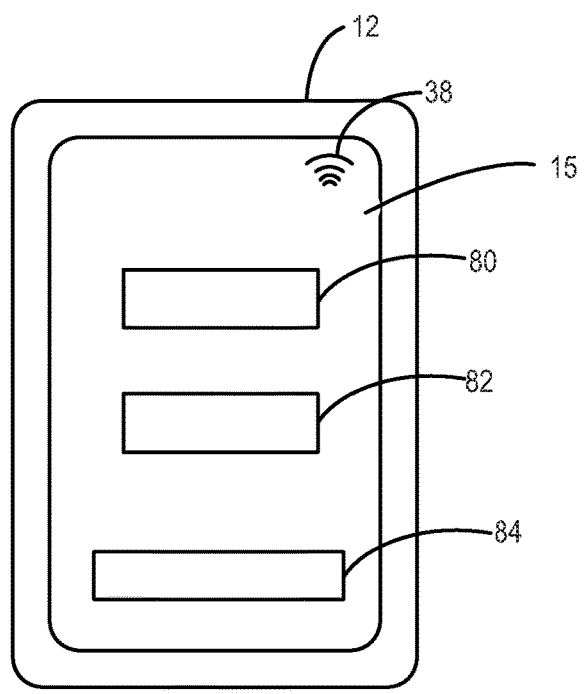

FIG. 1E shows a schematic diagram of another example user interface of the patient's device 12. Specifically, the display screen 15 shown in FIG. 1E shows a therapy selection screen. The display screen includes a sleep input button 80, an awake input button 82, and an appointment button 84. As described above, a user or patient may use the patient's device in sleep or awake mode. A healthcare professional may instruct the patient as to which therapy mode to use when assigning a tinnitus therapy protocol. Additionally, the appointment button 84 allows the patient's device 12 to be connected (e.g., wirelessly connected) with the healthcare professional's device 10 in order to generate, analyze, and/or adjust a tinnitus therapy. Thus, the display screen 15 shown in FIG. 1E may be an initial screen viewed by the patient before either starting the tinnitus therapy or connecting to a healthcare professional's device to create and/or adjust the tinnitus therapy.

As described above, the system of FIGS. 1A-1E provide for a tinnitus therapy system, comprising one or more physical, non-transitory, devices configured to hold data and/or instructions executable by a logic subsystem to generate a tinnitus therapy sound based on a tinnitus therapy sound type selected by a user from a set of pre-defined tinnitus therapy sound templates. The generated tinnitus therapy sound may further be based on one or more of an intensity and frequency level of the selected tinnitus therapy sound template selected by the user. In one example, a first physical, non-transitory, device of the one or more physical, non-transitory, devices includes a user interface, such that the user interface includes a plurality of input buttons for selecting sound parameters. Additionally, the data and/or instructions are further executable to receive a patient's audiogram data, and to send the generated tinnitus therapy sound to a second physical, non-transitory, device of the one or more physical, non-transitory, devices. In an additional example, the second physical, non-transitory, device includes one or more intensity controls for adjusting an intensity of the generated tinnitus therapy sound. Further, the data and/or instructions on the second physical, non-transitory, device are executable to play the generated tinnitus therapy sound repeatedly without breaks and track intensity adjustments to the generated tinnitus therapy sound over time.

Figure 2:
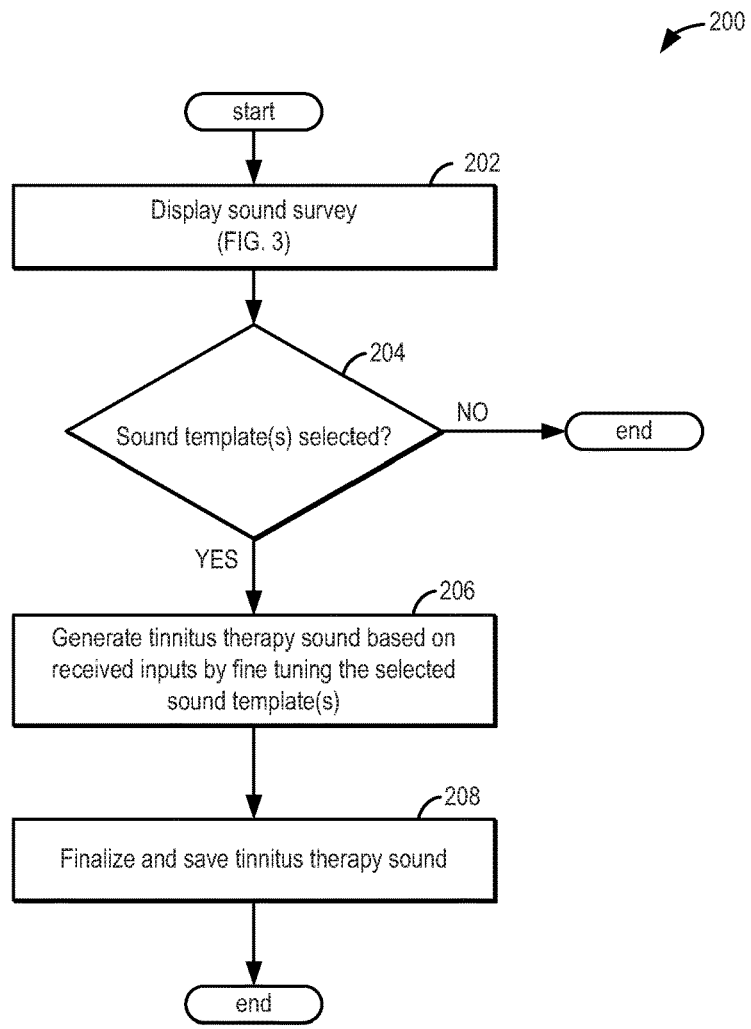
FIG. 2 shows an example method for generating a tinnitus therapy including a healthcare professional's device.

FIG. 2 shows an example method 200 for generating a tinnitus therapy using instructions stored on and executed by a logic subsystem of a healthcare professional's device, as explained with regard to FIGS. 1A-1D. For example, a healthcare professional's device may include tinnitus sound templates, the tinnitus sound templates including tinnitus therapy sound types, in order to generate a tinnitus therapy sound (e.g., tinnitus sound match). As such, the healthcare professional's device may be used to generate a tinnitus therapy based on the selected tinnitus therapy sound templates and adjustments made to the selected tinnitus therapy sound templates and/or the tinnitus therapy sound.

The method 200 begins at 202 where a sound survey is displayed. The method at 202 may further include completing the sound survey. In one example, completing the sound survey may include receiving inputs via inputs (e.g., adjustment buttons) displayed on the user interface via the display screen. For example, the sound survey may include a hearing threshold data input and the selection of sound templates. In another example, the sound survey may include a hearing test. The hearing test may include generating an audiogram based on the hearing test data. The method at 202 for completing the sound survey is shown in further detail at FIGS. 3A-3B. In one example, the tinnitus sound templates may include two or more of a cricket noise sound template, a white noise sound template, a pink noise sound template, a pure tone sound template, a broad band noise sound template, an amplitude modulated sine wave template, and a combination pure tone and broad band noise sound template. In an additional example, the sound templates selected may be a combination of at least two tinnitus therapy sound templates.

At 204, the method includes determining if the tinnitus therapy sound template(s) have been selected. Once the template(s) are selected, at 206, a tinnitus therapy sound may be generated based on the sound survey and adjustments made to the frequency and intensity inputs. Herein, a tinnitus therapy sound may also be referred to as a tinnitus therapy sound match and/or tinnitus sound match. Methods for adjusting each tinnitus sound template (e.g., for each tinnitus sound type) are shown at FIGS. 4-8, described further below. In one example, a single tinnitus therapy sound template may be selected and subsequently the tinnitus therapy sound template may be adjusted. Specifically, two tinnitus therapy sound templates may be selected. As such, a first tinnitus therapy sound template and a second tinnitus therapy sound template may be adjusted separately. For example, generating a tinnitus sound may include adjusting firstly a white noise sound template and secondly a pure tone sound template. In another example, a first tinnitus therapy sound template and a second tinnitus therapy sound template may be adjusted simultaneously. In this way, generating a tinnitus sound may include adjusting a white noise sound template and a pure tone sound template together. Once the adjustments to the tinnitus therapy sound template(s) are made, the tinnitus sound templates may be combined to make a specific tinnitus therapy sound. In one example, a generated tinnitus therapy sound may be played to a user to determine if the tinnitus therapy sound resembles the patient's perceived tinnitus. The generated tinnitus therapy sound may need additional adjustments and a first and/or second tinnitus therapy sound template may be re-adjusted. A tinnitus therapy sound may be generated following the additional adjustments of the tinnitus therapy sound template(s).

Further, generating a tinnitus therapy sound may, also include adjusting firstly a white noise sound template and secondly a broad band noise sound template. In an additional example, generating a tinnitus sound match may include adjusting firstly a pure tone sound template and secondly a broad band noise sound template. In another example, generating a tinnitus sound match may include adjusting firstly a cricket noise sound template and secondly a white noise sound template.

Additionally, generating a tinnitus sound match may include three or more tinnitus therapy sound templates. As such, a combined tinnitus therapy sound match may include, in one example, adjusting firstly a pure tone sound template, secondly a broad band noise sound template, and thirdly a white noise sound template. In another example, a combined tinnitus therapy sound match may include adjusting firstly a cricket noise sound template, secondly a broad band noise template, and thirdly a white noise sound template. In an additional example, a combined tinnitus therapy sound match may include adjusting firstly a white noise sound template, secondly a pure tone sound template, thirdly a broad band noise template, and fourthly a cricket noise sound template.

Further, therapy parameters may be added to the tinnitus therapy sound to finalize the tinnitus therapy sound. In one example, therapy parameters may include adding a help-to-sleep feature, setting the maximum duration of the tinnitus therapy, and allowing a user to adjust the volume during the tinnitus therapy. At 208, the tinnitus therapy sound may be saved and finalized. Once the tinnitus therapy sound is finalized, the tinnitus therapy is complete and may be sent to the patient's device. In one example, the healthcare professional's device is configured to hold instructions executable to send the generated tinnitus therapy sound to a second physical, non-transitory device (e.g., the patient's device). In another example, finalizing the tinnitus therapy sound includes assigning the generated tinnitus therapy sound to an individual patient of the individual patient audiogram. Assigning the tinnitus therapy sound also includes storing the generated tinnitus therapy sound with a code corresponding to the individual patient.

Figure 3A:
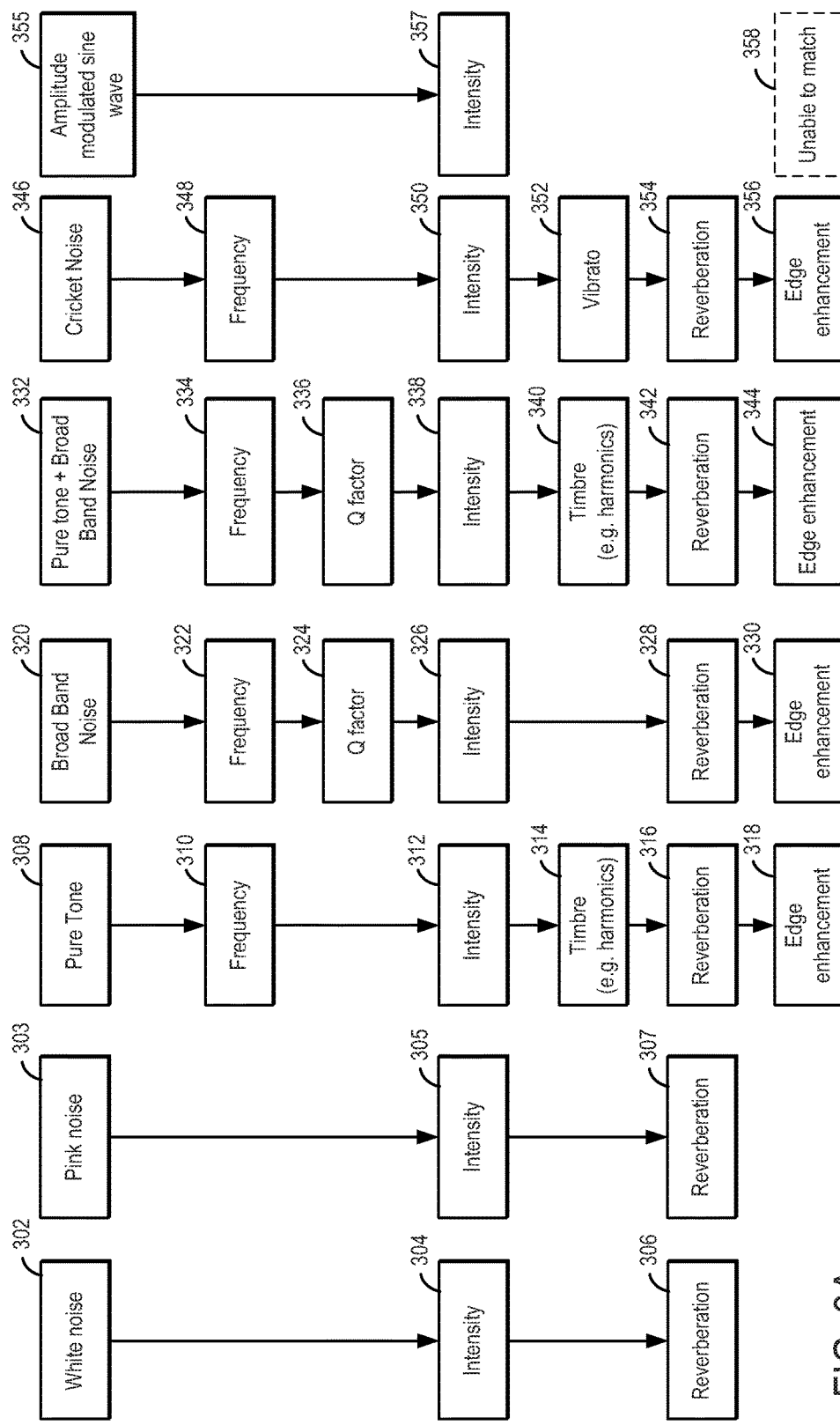
FIGS. 3A-3D show example methods for generating a sound survey including adjusting default tinnitus therapy sound templates.
Figure 3B:
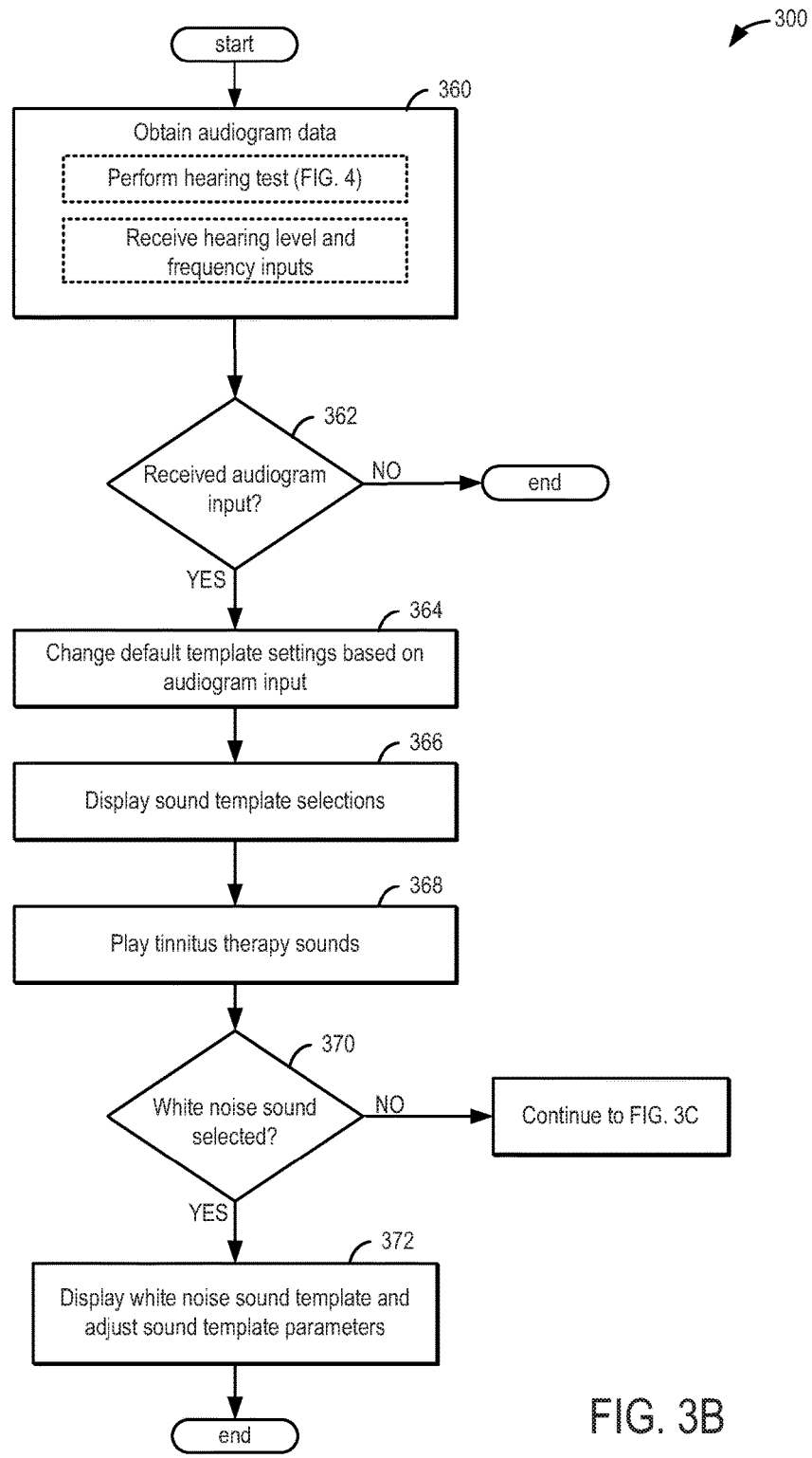
Figure 3C:
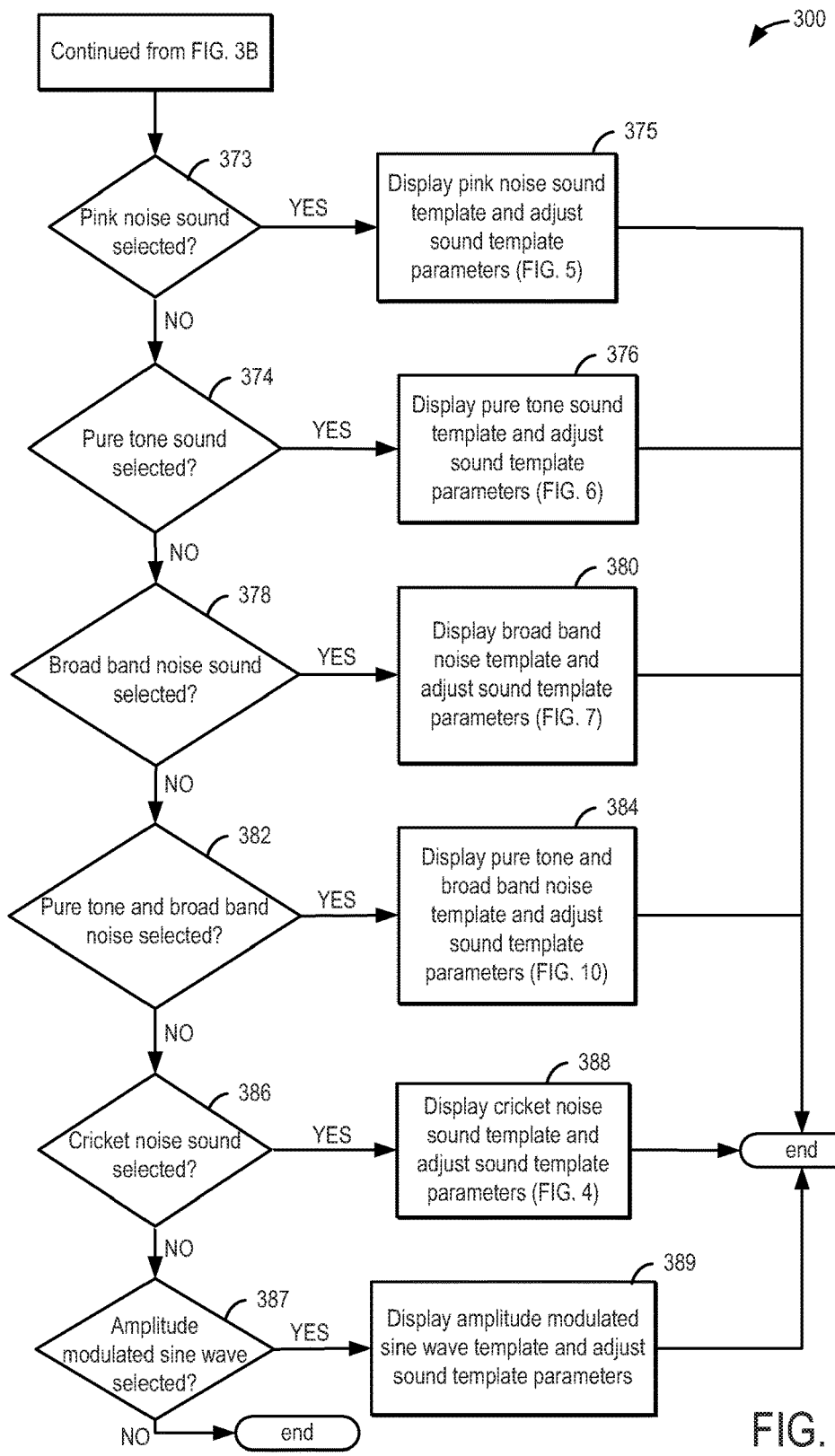

Now referring to FIGS. 3A-3C, an example method 300 for generating the sound survey, including adjusting tinnitus sound templates is shown. The sound survey may include inputting hearing threshold data determined by an audiogram and selecting tinnitus therapy sound templates in order to create a tinnitus therapy sound. As such, a tinnitus therapy sound template may be selected based on the similarity of the tinnitus therapy sound template (e.g. tinnitus sound type) to the patient's perceived tinnitus. The sound survey is an initial step in generating a tinnitus therapy sound such that the template(s) selected will be adjusted following the conclusion of the sound survey.

FIG. 3A shows example tinnitus therapy sound template selections including sound template adjustment parameters. Creating a tinnitus therapy may include presenting each of a white noise, a pink noise, a pure tone, a broad band noise, a combined pure tone and broad band noise, a cricket noise, and an amplitude modulated sine wave tinnitus therapy sound template to a user. In an alternate embodiment, creating a tinnitus therapy may include presenting a different combination of these sound templates to a user. For example, creating a tinnitus therapy may include presenting each of a white noise, a pink noise, a pure tone, a broad band noise, and a cricket noise tinnitus therapy sound template to a user. In yet another example, creating the tinnitus therapy may include presenting each of a white noise, a pure tone, and a combined tone tinnitus therapy sound template to a user. The combined tone may be a combination of at least two of the above listed sound templates. For example, the combined tone may include a combined pure tone and broad band noise tinnitus therapy sound template.

After playing each of the available tinnitus therapy sound templates, the user may select which sound type, or sound template, most resembled their perceived tinnitus. In this way, generating a tinnitus therapy sound may be based on the tinnitus therapy sound template selected by the user. After selecting one or more of the tinnitus therapy sound templates, the selected sound template(s) may be adjusted to more closely resemble the patient's perceived tinnitus. Adjusting the tinnitus therapy sound, or tinnitus therapy sound template, may be based on at least one of a frequency parameter and an intensity parameter selected by the user. As discussed above, a tinnitus therapy sound template(s) may be selected if the tinnitus therapy sound(s) resembles the perceived tinnitus sound of a patient. However, in one example, a patient's perceived tinnitus sound may not resemble any of the tinnitus therapy sound templates. As such, at 358, an unable to match input may be selected. Upon selection of an individual tinnitus therapy sound template, a tinnitus therapy sound template may include adjustment inputs including adjustments for frequency, intensity, timbre, Q factor, vibrato, reverberation, and/or white noise edge enhancement. The pre-determined order of adjustments of the tinnitus therapy sound template(s) selections are described below with regard to FIG. 3A.

FIG. 3A begins at 302, by selecting a white noise sound template. White noise sound template adjustments may include, at 304, adjustments for intensity and adjustments for reverberation, at 306. For example, adjusting the tinnitus therapy sound may be first based on the intensity parameter and second based on a reverb input when the tinnitus therapy sound template selected by the user is the white noise tinnitus therapy sound template. If a pink noise template is selected at 303, the pink noise sound template may be adjusted based on intensity at 305 and reverberation at 307. Adjustments to the pink noise sound template may be similar to adjustments to the white noise sound template. For example, adjusting the tinnitus therapy sound may be first based on the intensity parameter and second based on a reverb input when the tinnitus therapy sound template selected by the user is the pink noise tinnitus therapy sound template. In another example, a pure tone sound template, at 308, may be selected. A pure tone sound template may be adjusted based on frequency, at 310, and intensity, at 312. In addition, a pure tone sound template may be further adjusted base on timbre, at 314. In one example, timbre may include an adjustment of the harmonics of a tinnitus therapy sound including an octave and/or fifth harmonic adjustments. Further, a pure tone sound template may be adjusted based on a reverberation, at 316, and a white noise edge enhancement, at 318. In one example, adjusting the tinnitus therapy sound may be first based on the frequency parameter, second based on the intensity parameter, third based on one or more timbre inputs, further based on a reverberation (e.g., reverb) input, and fifth based on an edge enhancement input when the tinnitus therapy sound template selected by the user is the pure tone sound template. In another example, a white noise edge enhancement may be a pre-defined tinnitus therapy sound template. Herein, a white noise edge enhancement sound template may be referred to as a frequency windowed white noise sound template. Additionally, a white noise edge enhancement adjustment may include adjusting the frequency windowed white noise based on an intensity input.

Continuing with FIG. 3A, a broad band noise sound template, at 320, may be selected. A broad band noise sound template may include an adjustment for frequency, Q factor, and intensity, at 322, 324, and 326, respectively. Further adjustments to a broad band noise sound template may include reverberation, at 328, and white noise edge enhancement, at 330. For example, adjusting the tinnitus therapy sound may be first based on the frequency parameter, second based on a Q factor input, third based on the intensity parameter, fourth based on a reverberation input, and fifth based on an edge enhancement input when the tinnitus therapy sound template selected by the user is the broad band noise tinnitus therapy sound template.

At 332, a combination tinnitus sound template may be selected. A combination tinnitus sound template may include both a pure tone and a broad band noise sound. As such, the combination pure tone and broad band noise sound template may include adjustments for frequency, Q factor, and intensity, at 334, 336, and 338, respectively. A combination pure tone and broad band noise sound template may include further adjustments for timbre, reverberation, and white noise edge enhancement, at 340, 342, and 344, respectively. For example, adjusting the tinnitus therapy sound may be first based on the frequency parameter, second based on a Q factor input, third based on the intensity parameter, fourth based on a timbre input, fifth based on a reverberation input, and sixth based on an edge enhancement input when the tinnitus therapy sound template selected by the user is the combined pure tone and broad band noise tinnitus therapy sound template.

At 346, a cricket noise sound template may be selected. A cricket noise sound template may include adjustments for frequency, at 348, and intensity, at 350. Further adjustments to a cricket noise template may include a vibrato adjustment, at 352. A vibrato adjustment may include adjustment to the relative intensity of the cricket noise sound template. A cricket noise sound template may also include adjustments for reverberation, at 354, and white noise edge enhancement, at 356. For example, adjusting the tinnitus therapy sound may be first based on the frequency parameter, second based on the intensity parameter, third based on a vibrato input, fourth based on a reverberation input, and fifth based on an edge enhancement input then the tinnitus therapy sound template selected by the user is the cricket noise tinnitus therapy sound template.

At 355, an amplitude modulated sine wave sound template may be selected. In one example, the amplitude modulated sine wave template may include a base wave and carrier wave component. Additionally, the amplitude modulated sine wave template may include adjustments for intensity (e.g., amplitude) at 357, or alternatively adjustment to the base wave frequency. In alternate embodiments, additional or alternative adjustments may be made to the amplitude modulated sine wave sound template.

In another embodiment, the tinnitus therapy sound template(s) may include a plurality of tinnitus therapy sounds including but not limited to the tinnitus therapy sounds mentioned above with regard to FIG. 3A. For example, FIG. 3A may include alternative or additional sound templates which may be displayed and played for the user. Specifically, in one example, an additional combination tinnitus sound template may be presented to and possibly selected by the user. In one example, the additional combination tinnitus therapy sound template may include a combined white noise and broad band noise sound template. In another example, the additional combination tinnitus therapy sound template may include a template combining more than two tinnitus therapy sound types.

It should be appreciated that once a user selects a sound template and its properties (such as intensity or frequency), no additional modulation is applied to the selection. Further it should be appreciated that once a user selects a sound level, treatment or therapy where the selected sound is replayed occurs at the selected sound level without lowering.

Referring now to FIG. 3B, method 300 begins at 360 by obtaining audiogram data via an audiogram input and/or patient hearing data. The audiogram input may include hearing threshold data. In one example, the hearing threshold data may be determined at an earlier point in time during a patient audiogram. An individual patient's hearing threshold data may include decibel and frequency data. As such, the frequency, expressed in hertz (Hz), is the "pitch" of a sound where a high pitch sound corresponds to a high frequency sound wave and a low pitch sound corresponds to a low frequency sound wave. In addition, a decibel (dB) is a logarithmic unit that indicates the ratio of a physical quantity relative to an implied reference level such that the physical quantity is a sound pressure level. Therefore, the hearing threshold data is a measure of an individual patient's hearing level or intensity (dB) and frequency (Hz). Additionally, the audiogram input and/or patient hearing data may be received by various methods. In another example, a user interface may prompt a user to perform a hearing test in order to obtain audiogram data, as described below. Based on a generated audiogram from the hearing test, a user may input hearing level and frequency data when prompted by the user interface. In yet another example, the audiogram input of patient hearing data may be uploaded to the healthcare professional's device via a wireless network, a portable storage device, or another wired device. In another example, the audiogram or patient hearing data may be input by the user (e.g., medical provider) with the user interface of the healthcare professional's device.

At 362, the method includes determining if the hearing threshold data from the audiogram has been received. Once the audiogram data has been received, at 364, the initial tinnitus therapy sound template settings (e.g., frequency and intensity) may be modified by the hearing threshold data from an individual patient's audiogram. For example, in order for the tinnitus therapy sound template to be in the correct hearing range of an individual patient, specific frequency and intensity ranges may not be included in the tinnitus therapy sound template. Specifically, if an audiogram's hearing threshold data reflects mild hearing loss of a patient (e.g., 30 dB, 3000 Hz), the frequency and intensity range associated with normal hearing will be eliminated from the template default settings (e.g., 0-29 dB; 250-2000 Hz) such that a default setting starts at the hearing level of the patient. In one example, an audiogram may include a range of frequencies including frequencies at 125 Hz, 250 Hz, 500 Hz, 1000 Hz, 2000 Hz, 3000 Hz, 4000 Hz, 6000 Hz, 8000 Hz, 10,000 Hz, 12,000 Hz, 14,000 Hz, 15,000 Hz, and/or 16,000 Hz.

Additionally, the hearing threshold data from an individual patient's audiogram may be used to determine sensitivity thresholds (e.g., intensity and frequency) of the tinnitus therapy sound. For example, hearing threshold data may include maximum intensity and frequency thresholds for an individual patient such that the tinnitus therapy sound template's intensity and/or frequency may not be greater than a patient's sensitivity threshold. As such, the sensitivity levels will further limit the intensity and frequency range of the tinnitus therapy sound template. As such, the frequency and intensity range of the tinnitus therapy sound template may be based on the hearing level and hearing sensitivity of the patient. Therefore, at 364, the tinnitus therapy sound template(s) default settings are adjusted to reflect the audiogram, hearing threshold data, and hearing sensitivity of the patient.

At 366, a plurality of tinnitus therapy sound templates may be displayed. In one example, the tinnitus therapy sound templates may include tinnitus sounds including cricket noise, white noise, pink noise, pure tone, broad band noise, amplitude modulated sine wave sound, and a combination of pure tone and broad band noise. Specifically, each tinnitus therapy sound template may be pre-determined to include one of the above listed tinnitus sounds having pre-set or default sound characteristics or template settings (e.g., frequency, intensity, etc.). As described above, in other examples more or less than 6 different tinnitus therapy sound templates may be displayed.

At 368, the tinnitus therapy sound template selection process begins by playing pre-defined tinnitus therapy sounds (e.g., sound templates). In one example, the pre-defined tinnitus therapy sounds may be played in a pre-determined order including playing a white noise sound first followed by a pink noise sound, pure tone sound, a broad band sound, a combination pure tone and broad band sound, a cricket noise sound, and amplitude modulated sine wave sound. In another example, the tinnitus therapy sounds may be played in a different order. Further, the different tinnitus therapy sounds may either be presented/played sequentially (e.g., one after another), or at different times. For example, the sound templates may be grouped into sound categories (e.g., tonal or noise based) and the user may be prompted to first select between two sound templates (e.g., cricket and white noise). Based on the user's selection, another different pair of sound templates (or tinnitus therapy sounds) may be displayed and the user may be prompted to select between the two different sound templates. This process may continue until one or more of the tinnitus therapy sound templates are selected. In this way, the method 300 may narrow in on a patient's tinnitus sound match by determining the combination of sound templates included in the patient's perceived tinnitus sound.

Figure 3D:
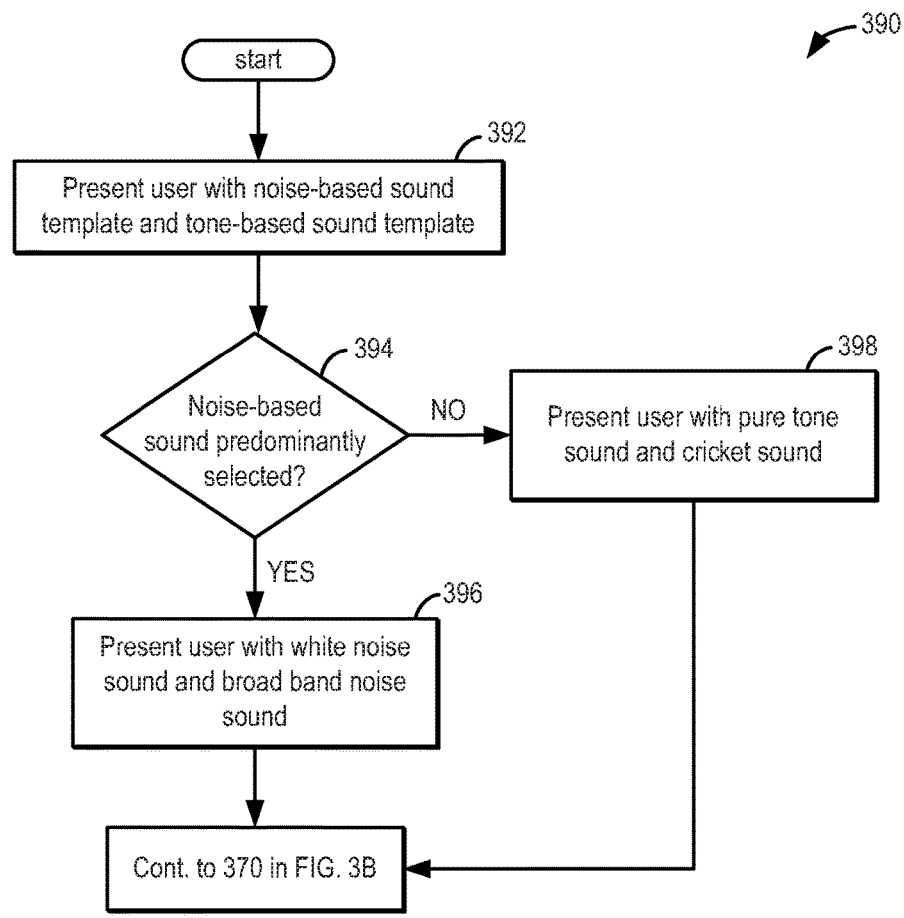

FIG. 3D presents an example method 390 of an order of presenting the different tinnitus therapy sounds (e.g., sound templates) to the user. As such, method 390 may be performed during step 368 in method 300. At 392, the method includes presenting a user, via a user interface of the healthcare professional's device, with a noise-based sound template and a tone-based sound template. The noise-based sound template may be a white noise sound template, a broad band noise sound template, a pink noise sound template, or some combination template of the white noise, broad band noise, and/or pink noise sound templates. The tone-based sound template may be a pure tone sound template, a cricket sound template, or some combined pure tone and cricket sound template.

At 394, the method includes determining if the noise-based sound was predominantly selected. In one example, the noise-based sound may be predominantly selected if an input selection of the noise-based sound is received. In another example, the user interface of the healthcare professional's device may include a sliding bar between the noise-based and tone-based sounds. In this example, the noise-based sound may be predominantly selected if an input (e.g., a sliding bar input) is received indicating the tinnitus sound is more like the noise-based sound than the tone-based sound. If an input of a predominantly noise-based sound is received, the method continues on to 396 where the method includes presenting the user with a white noise sound, a pink noise sound, and/or a broad band noise sound. The method then returns 370 in FIG. 3B. In one example, a patient may be presented with two different noise based sounds and then be able to use a slide bar to select whether the tinnitus sound sounds more like a first sound or a second sound. It should be appreciated that the sound may be selected for the left or the right or both. Conversely at 394, if the noise-based sound is not predominantly selected, the method continues on to 398 to present the user with a pure tone sound and a cricket sound. The method then returns to 370 in FIG. 3B. Other methods of presenting the different sound types (e.g., templates) to a user are possible and may include presenting the sound templates in different combinations and/or orders.

Following the presentation of the tinnitus therapy sound template, the user interface of the healthcare professional's device will display a prompt to the user confirming the tinnitus therapy sound template selection. For example, confirming the tinnitus therapy sound template selection may include selecting whether the selected sound template is similar to the patient's perceived tinnitus. At 370, the method 300 includes determining if a white noise sound is selected. In one example, a white noise sound may be selected if the presented white noise sound resembles a patient's perceived tinnitus. At 370, if a white noise sound is selected as a tinnitus sound similar to that of the patient's, the method continues on to 372 to display a white noise sound template. In one example, upon selection of a tinnitus therapy sound template, a tinnitus sound, corresponding to the selection, will be presented to the user. Following the presentation of the tinnitus therapy sound template, a user interface will display a prompt to the user confirming the tinnitus therapy sound template selection (e.g., white noise sound template). Once the tinnitus therapy sound template is selected, the user interface will display the tinnitus therapy sound template on the tinnitus therapy sound screen.

Method 300 continues to 373 in FIG. 3C where the method includes determining if a pink noise sound template is selected. If a pink noise sound template is selected as a tinnitus sound similar to that of the patient's, the method continues to 375 to display a pink noise sound template. If pink noise is not selected, the method continues on to 374 where the method includes determining if a pure tone sound template is selected. If a pure tone sound template is selected as a tinnitus sound similar to that of the patient's, at 376, the pure tone sound template is displayed in the and further adjustment to the pure tone sound template may be made. If a pure tone sound is not selected, at 378, the method includes determining if a broad band noise sound is selected. If a broad band sound template is selected as a tinnitus sound similar to that of the patient's, at 380, the broad band noise sound template is displayed and further adjustment to the broad band noise sound template may be made.

If a broad band noise sound is not selected, at 382, the method includes determining if a combination of pure tone and broad band noise sound is selected. If a combination of pure tone and broad band noise sound template is selected as a tinnitus sound similar to that of the patient's, at 384, the combination pure tone and broad band noise sound template is displayed and further adjustment to the combination pure tone and broad band noise sound template may be made.

If a combination of pure tone and broad band noise sound is not selected, at 386, the method includes determining if a cricket noise sound is selected. In one example, the user interface of the healthcare professional's device will prompt a user to select a cricket noise sound template. If the cricket noise sound template is selected, at 388, a user interface will display a cricket noise sound template.

If the cricket noise sound template is not selected at 386, the method continues to 387 to determine if an amplitude modulated sine wave template is selected. If the amplitude modulated sound template is selected, at 389, a user interface will display the amplitude modulated sine wave template. A user may then adjust an intensity and/or additional sound parameters of the sine modulated sine wave template. After any user inputs or adjustments, the method may include finalizing the tinnitus therapy sound including the amplitude modulated sine wave template.

An individual patient's perceived tinnitus may incorporate a plurality of tinnitus sounds; therefore, the method 300 may be repeated until all required templates have been selected. For example, a patient's perceived tinnitus may have sound characteristics of a combination of tinnitus sounds including white noise and broad band noise, white noise and pure tone, or pure tone and broad band noise. In yet another example, the patient's perceived tinnitus may include sound characteristics of two or more tinnitus sounds including two or more of white noise, pink noise, broad band noise, pure tone, amplitude modulated sine wave, and cricket. Additionally, the tinnitus therapy sound generated based on the selected tinnitus therapy sound templates may contain different proportions of the selected sound templates. For example, a generated tinnitus therapy sound may contain both pure tone and cricket sound components, but the pure tone component may make up a larger amount (e.g., 70%) of the combined tinnitus therapy sound. As such, two or more tinnitus therapy sound templates may be selected during the template selection process. In one example, a first tinnitus therapy sound template may include a white noise sound and a second tinnitus therapy sound template selection may include a pure tone sound. In another example, a first tinnitus therapy sound template may include a broad band noise sound template and a second tinnitus therapy sound template may include a white noise sound template. In another example, the first tinnitus therapy sound template may include a pure tone sound and a second tinnitus therapy sound template may include a broad band noise sound. In another example, a first tinnitus therapy sound template may include a cricket noise sound and a second tinnitus therapy sound template may include a white noise sound template.

In an additional example, a first tinnitus therapy sound template may include a pure tone sound template, a second tinnitus therapy sound template may include a broad band noise sound template, and a third tinnitus therapy sound template may include a white noise sound template. In another example, a first tinnitus therapy sound template may include a cricket noise sound template, a second tinnitus therapy sound template may include a broad band noise template, and a third tinnitus therapy sound template may include a white noise sound template. In an additional example, a first tinnitus therapy sound template may include a white noise sound template, a second tinnitus sound template may include a pure tone sound template, a third tinnitus therapy sound template may include a broad band noise template, and a fourth tinnitus therapy sound template may include a cricket noise sound template. After receiving one or more tinnitus therapy template selections, the selected tinnitus therapy template(s) may then be individually or simultaneously adjusted, to create the tinnitus therapy sound.

Figure 4:
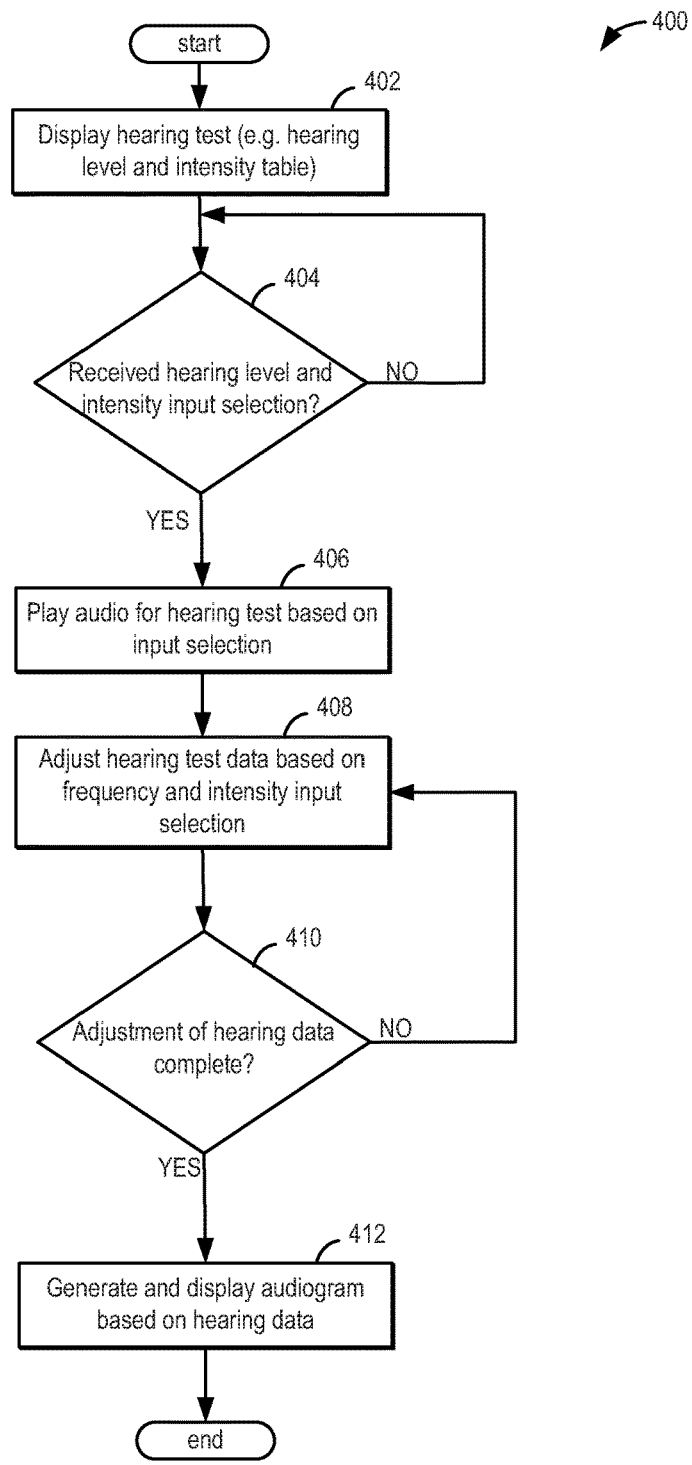
FIG. 4 shows an example method for generating an audiogram including performing a hearing test.

Now referring to FIG. 4, an example method 400 for generating an audiogram is shown including performing a hearing test. A hearing test may be performed during a sound survey including the tinnitus therapy sound template selection process, as described above with reference to FIGS. 3B-3D. Further, the hearing test data may be used to generate an audiogram. A patient's audiogram may be used to set the pre-defined frequency and intensity parameters of the tinnitus therapy sound template(s).

At 402, the method includes displaying a hearing test for a user. In one example, a hearing test may include a hearing level and intensity table. The hearing level and intensity table may include a plurality of inputs including hearing level or intensity inputs and frequency inputs. In another example, the hearing level and intensity table may include a range of frequencies and intensities. At 404, the method includes determining if a hearing level and frequency input selection has been received. If an input selection has not been received, the method continues to display the hearing test. However, if a frequency and intensity input has been received, at 406, the method includes playing a pre-determined sound based on an input selection. In one example, if a user selects a frequency input and an intensity input, a corresponding sound may be presented to the user. In another example, a user interface may prompt a user to confirm if the sound played is within a user's hearing range. The method, at 408, includes adjusting the hearing test based on user frequency and intensity input selection. In one example, a hearing level and intensity table may be adjusted to include a range of frequencies and intensities based on the user selection. For example, frequencies and intensities that are not in the range of the user's hearing levels might not be available for selection by the user.

Figure 13:
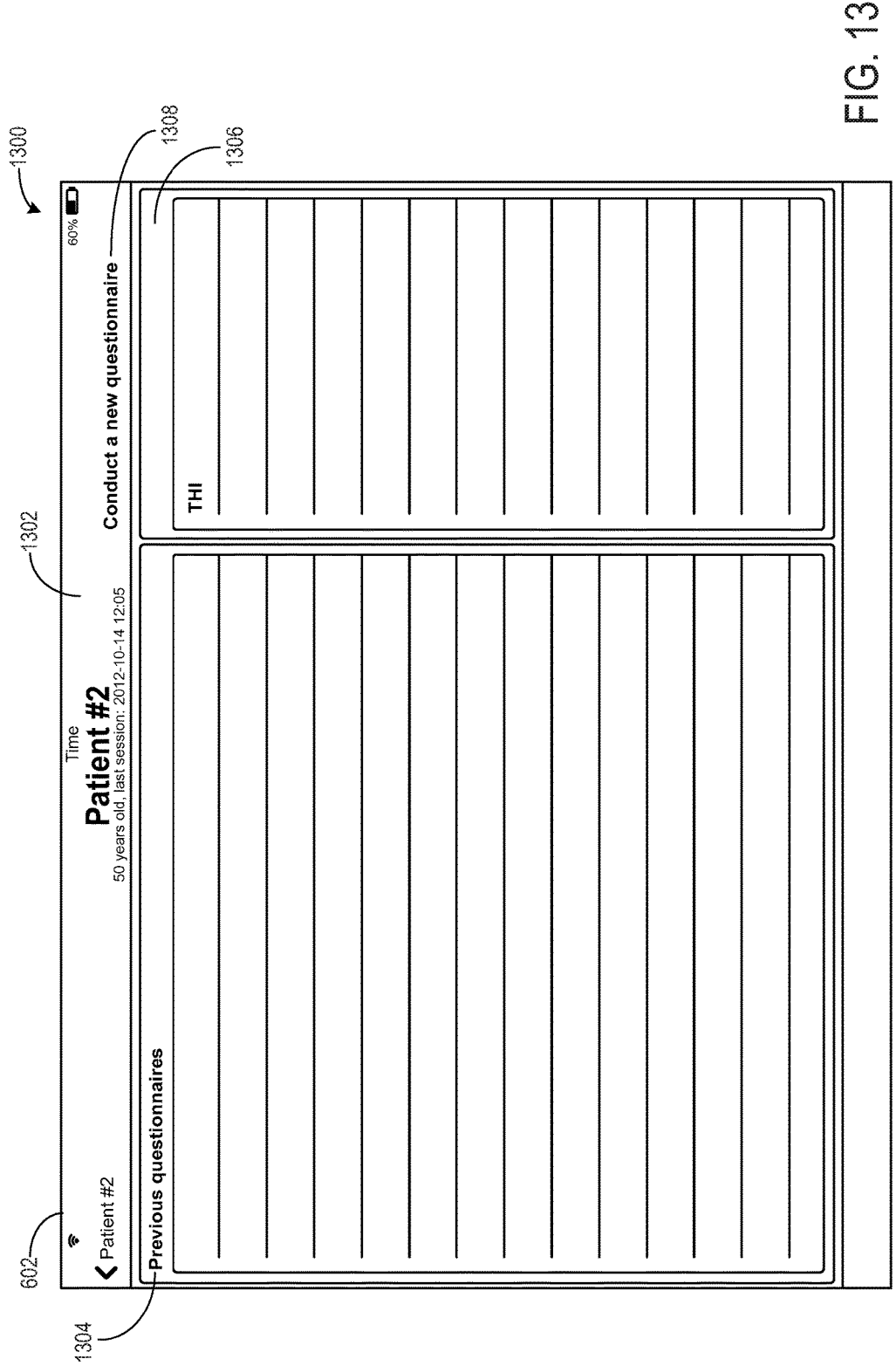
FIG. 13 shows a schematic of a user interface for displaying patient questionnaires including hearing tests.

At 410, the method includes determining if the adjustment of the hearing data is complete. If the adjustment is not complete, the method continues, at 408, until the adjustment to the hearing data is completed. The method, at 412, includes generating and displaying an audiogram based on the adjusted hearing data. In one example, based on the user selected inputs, an audiogram might be displayed. An audiogram may include the hearing level and frequency of a patient. In another example, the generated audiogram may be used in the tinnitus therapy sound template selection. Further, the audiogram data may be used to set the pre-defined frequency and intensity levels of the tinnitus therapy sound template, as described above with reference to FIGS. 3B-3D. Additionally, the audiogram data and/or hearing test results may be stored in the healthcare professional's device and accessed via a questionnaires screen of the healthcare professional's device (as shown in FIG. 13, discussed further below), the questionnaires screen including a list of any completed hearing tests.

FIGS. 5A-5B show an example method 500 for recording and tracking patient data. Method 500 further includes presenting the tracked data to a user and adjusting the tinnitus therapy based on the tracked data. Once a tinnitus therapy sound match (e.g., tinnitus therapy sound) is generated and uploaded onto a patient's device, a patient may be instructed to use the patient's device over a set duration of time. In one example, a patient's device may include data and/or instructions that are executable to play the generated tinnitus therapy sound repeatedly without breaks. In addition, the patient's device may record all performed actions to the device during usage. In one example, the patient's device may also track intensity adjustments to the generated tinnitus therapy sound over time. In this way, a physician may review and track the recorded data, thereby determining the progress of the tinnitus therapy. In addition, the accumulation of an individual patient's tracked data may generate a medical record including a patient audiogram, the tinnitus therapy sound, and a patient adjusted tinnitus therapy sound.

In some embodiments, the patient or user may have one or more tinnitus sound matches (e.g., one or more generated tinnitus therapy sounds). For example, more than one tinnitus sound match may be generated and assigned to a single patient. In another example, the patient may adjust (e.g., alter) their sound match using the process described above in FIGS. 3A-3D on a device at home (e.g., the same or similar to the healthcare professional's device). In this way, the patient may generate and/or modify their tinnitus sound match to create new sound matches different than their original sound match. The patient may then choose to play any of their generated tinnitus sound matches based on changes to their perceived tinnitus sound and/or based on an indication from a healthcare professional. For example, the patient may listen to different tinnitus sound matches on different nights or during different sessions.

At 502, the method includes determining if a therapy session has started. In one example, a therapy session may not begin until a start button input is selected on the patient's device (e.g., start therapy input button 40 shown in FIG. 1A). Once the therapy session has started, at 504, therapy data from the patient's device may be recorded for the duration of the therapy session. In one example, recorded data may include a patient's information, date of the therapy session, time of day the therapy session, and/or volume usage (e.g., changes in intensity). The recorded data may further include the specific tinnitus therapy sound match that was played during a session. This may include an identifier (e.g., match 1 or match 2) for each tinnitus sound match created by a user or patient. For example, upon creation of a tinnitus sound match, the sound match may be assigned a unique name and/or identifying information that identifies and differentiates the unique sound match from other sound matches for a same patient (or user). If a patient has more than one tinnitus sound match, the recorded data may include individual intensity changes for each sound match. In another example, the recorded volume usage may include changes in intensity to both right and left ear inputs. As such, a user may change the intensity of the tinnitus therapy sound match at the start of the therapy session as well as during the therapy session. In another example, the patient's device may be continuously playing the tinnitus therapy sound without breaks and tracking intensity changes to the continuously played tinnitus therapy sound over time.

At 506, the method includes determining if the therapy session has ended. For example, in order for a therapy session to end, a finish button input may be selected. Alternatively, the therapy session may end after a therapy duration has passed. If the session has not ended, recording of the therapy data may be continued. Once a finish input has been selected, at 508, the recorded therapy data may be saved and stored on the patient's device, at 510. Following the conclusion of a tinnitus therapy session, for example, a plurality of tinnitus therapy sessions may be played on a patient's device. Therefore, an accumulation of recorded data may be saved and stored on a patient's device. At 512, the recorded therapy data may be uploaded. In one example, the patient's device may receive a signal from a healthcare professional's device (e.g., tablet, desktop computer, etc.) to upload the recorded therapy data. As such, uploading the recorded data may occur wirelessly. In another example, the uploaded data may include date of the therapy session, time of day the therapy session was played, and changes in intensity (e.g., volume usage). In yet another example, therapy data may also include metadata from the patient's device. Further, at 514, the patient's identification information is uploaded to a healthcare professional's device. In one example, a plurality of recorded data may be uploaded to a healthcare professional's device. As such, a patient medical record (e.g., report) may be generated. In one example, generating a patient medical record may include a patient audiogram, the combined tinnitus therapy sound, and a patient adjusted tinnitus therapy sound.

Further, the uploaded recorded data may be stored and saved on a healthcare professional's device, thereby allowing a physician to track the recorded data over multiple therapy sessions. As such, tracking changes to the therapy session over a duration of time may determine patient progress to the tinnitus therapy. In one example, tracking changes of a patient's device may include remotely tracking intensity changes to the combined tinnitus therapy sound. In another example, tracking changes of a patient's device may include remotely transferring tracked changes to a secured data network.

The method continues to 516 in FIG. 5B where the method includes presenting the tracked therapy data to a user (e.g., a patient and/or healthcare professional). In one example, after a duration or a series of therapy sessions, a patient may have an appointment with a healthcare professional. Additionally or alternatively, a patient may view the tracked data on their own. In one example, presenting the tracked therapy data includes presenting each of a volume evolution (e.g., intensity changes) and usage data of the tinnitus sound match. The volume evolution may include changes in an overall, right ear, and/or left ear volume of the played tinnitus sound match (e.g., the volume of the sound match as listened to by the patient). Additionally, the volume evolution may be presented as volume changes over time or over a series of sessions. Usage data may include a frequency of use or frequency of listening to the sound match. For example, presenting the usage data may include one or more of presenting a total number of sessions, a date of a first session, a date of a last (e.g., most recent) session, an average session length, an average daily usage (e.g., in hours per day), and/or an average weekly usage (e.g., days per week). Presenting therapy data may also include presenting therapy details such as the tinnitus sound matches (e.g., all the different sound matches used by the patient) and prescribed therapy parameters such as the help-to-sleep option and the allow to adjust volume option. In one example, the tracked therapy data may be presented to the user via a user interface of the healthcare professional's device, such as the user interfaces shown in FIGS. 6-13, discussed further below. Tracking and viewing the changes made to the tinnitus therapy sound match over a duration of time may aid in determining patient progress with the tinnitus therapy.

Method 500 may further include, at 518, generating a report based on the tracked therapy data. In one example, the report may include a session report showing data for a particular (e.g., selected) session (e.g., one night of listening to the sound match). In another example, the report may include an evolution report, such as the evolution report shown in FIG. 14 and FIG. 15, described further below. The evolution report may present patient details, a volume evolution for a series of sessions, as well as usage data and sound match details (e.g., sound match composition such as pure tone or combined white noise and pure tone sound) for each session in the series of sessions. In one example, a healthcare professional may generate the report during an appointment with the patient. In another example, a user (e.g., patient) may create the report after tracking one or more therapy sessions.

In some examples, the tracked therapy data may be used to make changes to the generated tinnitus therapy sound match. Thus, at 520, the method may include adjusting the tinnitus therapy based on the tracked and presented therapy data. In one example, a user may adjust a patient's tinnitus sound match and/or therapy parameters of the tinnitus sound match based on the tracked data. More specifically, as one example, adjusting the tinnitus therapy may include changing one or more sound parameters of the tinnitus sound match. For example, intensity, frequency, or other sound parameters of one or more sound templates included in the tinnitus sound match may be adjusted. In another example, a new template may be added to the tinnitus sound match or another sound template may be removed from the tinnitus sound match. In another example, a new tinnitus sound match may be created including a different sound template than the original sound match. In yet another example, the prescribed duration of therapy, the day/night option, the help-to-sleep option, or the allow volume change option may be changed based on the tracked data. In this way, a user may utilize tracked data to guide tinnitus therapy changes in order to better treat the patient. In some examples, adjusting the tinnitus therapy may follow similar methods to those presented in FIGS. 3A-3D, as described above. By tracking patient therapy data over time and subsequently presenting the tracked data to a user, changes to (or the evolution of) a patient's tinnitus may be identified. Further, by adjusting the patient's tinnitus therapy (including the tinnitus sound match) based on the tracked therapy data, a more effective tinnitus treatment may be prescribed to the patient. As a patient's tinnitus continues to evolve over time, the tinnitus therapy may be updated to match a patient's perceived tinnitus sound and further reduce the patient's tinnitus.

In alternate embodiments, the methods presented above at FIGS. 1A-4 for generating a tinnitus therapy sound or match may also be used to generate a sound or match for therapy of other neurological disorders. For example, the generated audio sound may be at least partially used for treating neurological disorders such as dizziness, hyperacusis, misophonia, Meniere's disease, auditory neuropathy, autism, chronic pain, epilepsy, Parkinson's disease, and recovery from stroke. In this embodiment, sound templates may be adjusted based on patient data, the patient data being specific to the neurological disorder. In some examples, different combinations of the above described sound templates may be used to generate an audio sound or match for one of the neurological disorders.

The healthcare professional's device may allow a healthcare provider to manage one or more patients or users. For example, the healthcare professional's device may include one or more administrative or patient management screens (e.g., user interfaces or displays) that enabled the healthcare provider to select and then manage data of one or more patients. For example, a patient may be selected and statistics (e.g., tracked data) may be provided to show a patient's progress or data tracking for a single session or a plurality of sessions. Information regarding the patient or patient's tinnitus therapy may be inputted, tracked and in some examples linked with other records or databases, including but not limited to digital medical records.

Figure 14:
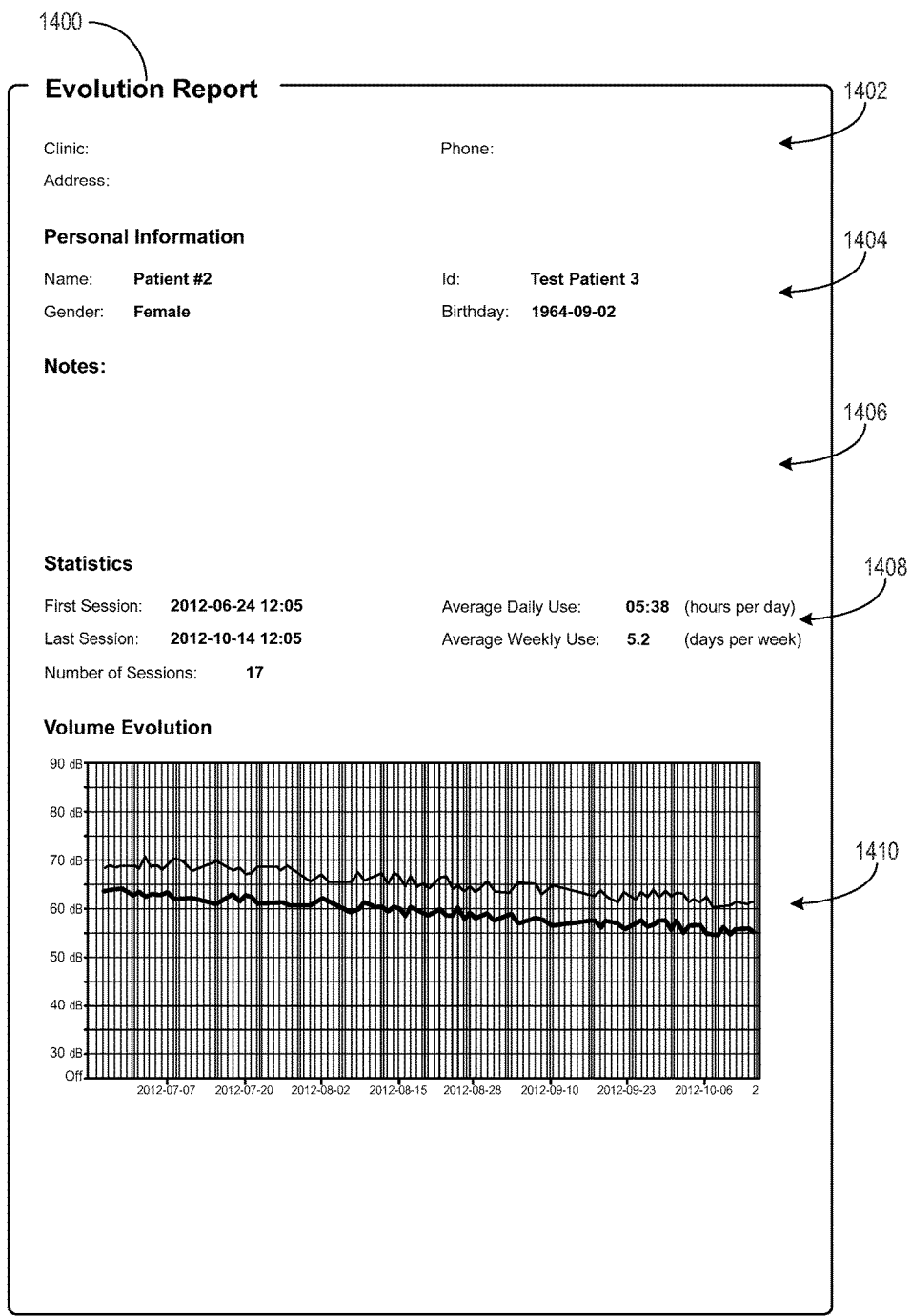

FIGS. 6-12 show example user interfaces for a healthcare professional's device for displaying and analyzing tracked data of a patient's tinnitus therapy. In one example, the tracked patient data may include one or more of a total number of therapy sessions (each session being a period of continuous use, without breaks, of listening to the tinnitus therapy sound match), a duration of each session, an average session duration, a frequency of the sessions, volume changes (e.g., volume evolution) to each tinnitus sound match or overall volume changes, etc. FIGS. 6-12 may include common inputs, buttons, boxes, or other interface elements and may only be described once. These common elements may be labeled similarly throughout the figures. FIG. 13 shows an example user interface for displaying patient questionnaires including hearing tests. Further, FIGS. 14-15 show schematics of a report generated from tracked data of a patient's tinnitus therapy. The report may be displayed on a user interface of the healthcare professional's device and then be either transferred to an alternate device (e.g., e-mailed or wireless sent to a patient's device), printed, or stored in an electronic patient record. The example user interfaces shown in FIGS. 6-15 may include similar parts and features as described above for the healthcare professional's device 10 shown at FIGS. 1A-1D. As such, descriptions of the similar features and/or components may be found above with reference to FIGS. 1A-1D. For example, the example user interfaces may correspond to the display screen 14 of the healthcare professional's device 10 shown in FIGS. 1A-1D. Further, the user interfaces may be used to at least partially perform the methods described above with reference to FIGS. 2-4. It should be appreciated that the user interfaces described and discussed herein are provided for illustrative purposes only, and are not intended to be limiting its scope.

Figure 6:
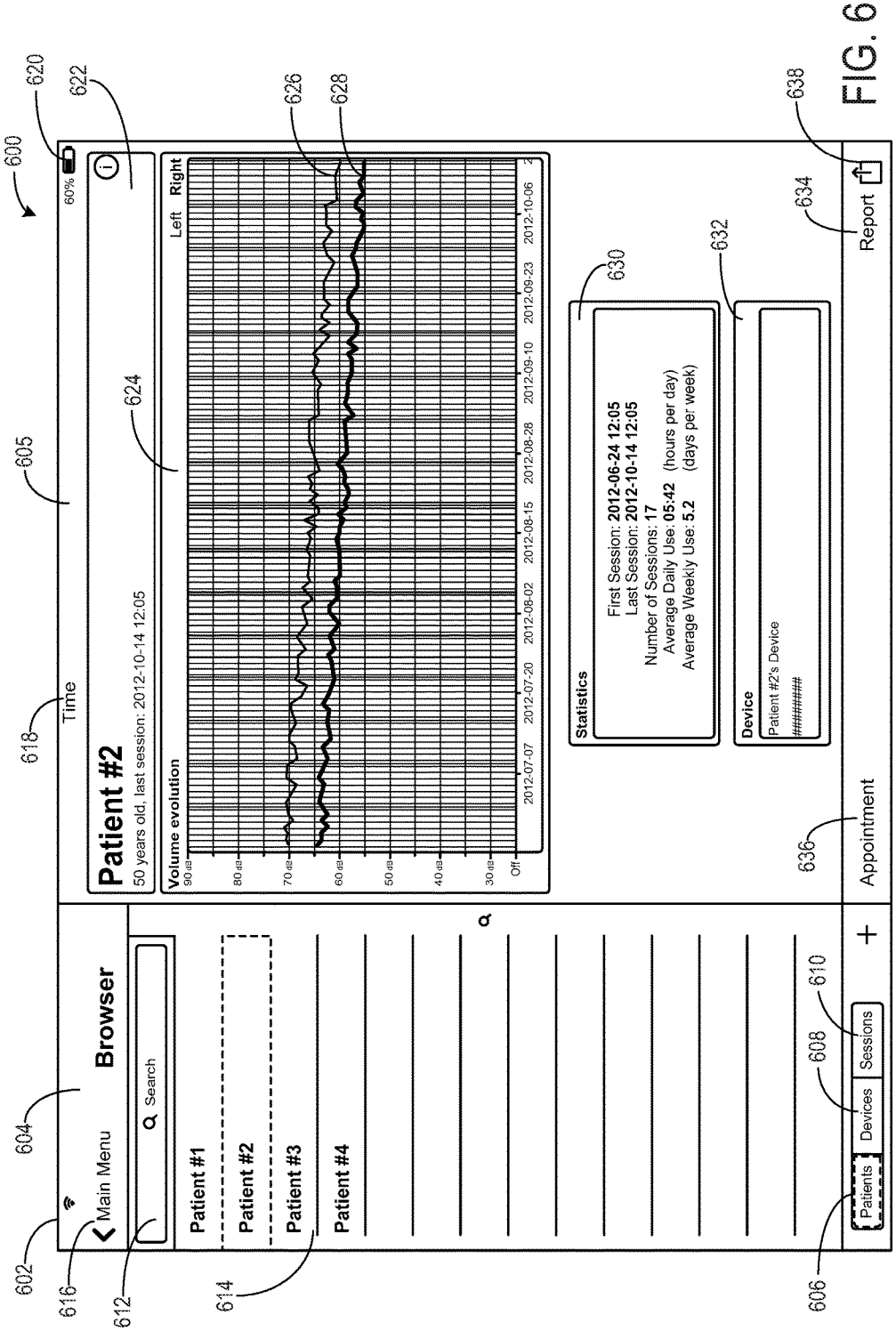
FIGS. 6-12 show schematic diagrams of a user interface for displaying tracked data of a patient's tinnitus therapy.

FIG. 6 shows a schematic 600 of a user interface 602 (e.g., display screen 14 of healthcare professional's device 10) displaying a patient overview screen 605. On one side of the display there is a browser screen 604. The browser screen 604 may be accessed from a main menu screen (not shown) and may allow a user to browse patients, devices and sessions. A user may return to the main menu screen by selecting the main menu input button 616. As shown in FIG. 6, the browser screen 604 includes a patients input button 606, a devices input button 608, and a sessions input button

610. Selecting any of these three input buttons may load the patient overview screen 605 (may also be referred to herein as a quick view screen). Selecting the devices input button 608 may allow a user to select a patient's device (e.g., a device external to the healthcare professional's device). Alternatively, a patient's data from a patient's device may be uploaded to the healthcare professional's device before beginning an analysis session. In one example, selecting the devices input button 608 may cause a list of devices that have been previously connected to the healthcare professional's device to appear. Alternatively, a name of the patient's device may be input into a search box 612. Further, the search box 612 may be used to search for a specific item (e.g., device, patient, or session) when a corresponding input button (e.g., device input button 608, patient input button 606, or session input button 610) is selected. After selecting a desired patient's device, the patient overview screen 605 will load and populate with data from the selected patient's device paired with the healthcare professional's device. In another example, if a patient's device has not been previously paired with the healthcare professional's device, another input button may enable pairing (e.g., wirelessly) between the two devices.

By selecting the patients input button 606 (as shown in FIG. 6), a patient list 614 may appear within the browser screen 604. The patient list may include a list of patients' full names (e.g., last and first names). Upon selecting a patient from the patient list 614, the patient overview screen 605 corresponding to the selected patient will appear on a side of the user interface 602. For example, as shown in FIG. 6, Patient #2 is selected in the patient list 614 and the data for Patient #2 is displayed in the patient overview screen 605.

Additionally, by selecting the sessions input button 610, a session list (shown in FIG. 7, described further below) may appear showing a list of sessions corresponding to a selected patient and/or device. Further, the user interface 602 may include a time display (e.g., current time) 618 and a battery display 620.

The patient overview screen 605 includes a patient's name and session data section 622. The patient's name and session data section 622 includes the patient's name, patient's age, and the date and time of the patient's last session (e.g., last period of listening to the tinnitus sound match and tracking patient data). The patient overview screen 605 further includes a volume evolution chart 624 displaying (e.g., presenting) volume changes (e.g., intensity changes) throughout the selected patient's therapy sessions. Specifically, the volume evolution chart 624 displays volume (e.g., in dB) on the y-axis and session date on the x-axis. Each therapy session may include a session where the tinnitus therapy sound match was played for a duration (e.g., played continuously for the duration). A first line 626 indicates the volume in the left ear and a second line 628 indicates the volume in the right ear. In some examples, the volume evolution chart may also include different colored (or shaded) columns that indicate different therapies. For example, if a patient changes the therapy during a session (e.g., changes the volume, tinnitus sound match, or another therapy parameter), a color change may appear on the chart. Additionally, a darker vertical line on the chart may indicate when an appointment occurred (e.g., an appointment with a healthcare professional).

The patient overview screen 605 also includes a statistics box 630. The statistic box 630 includes patient information unique to the selected patient including: date of a first session, date of a last session, total number of sessions, average daily use (e.g., in hours per day), and average weekly use (e.g., in days per week). In other embodiments, the statistics box 630 may include additional or alternative patient information. The patient overview screen 605 may include a device box 632 showing information specific to a patient's device. For example, the device box 632 may display a device name that the healthcare professional's device is paired with. A reports input 634 may also be displayed on the patient overview screen 605. The reports input 634 results in a session report or an evolution report to display, as shown in FIGS. 14-15, discussed further below. Further still, the patient overview screen 605 includes an appointment input 636 allowing a user to start a new patient session. Finally, the patient overview screen 605 may include a detail view input 638 resulting in a patient detail view screen to be displayed, as shown in FIGS. 7-9, described further below.

Figure 7:
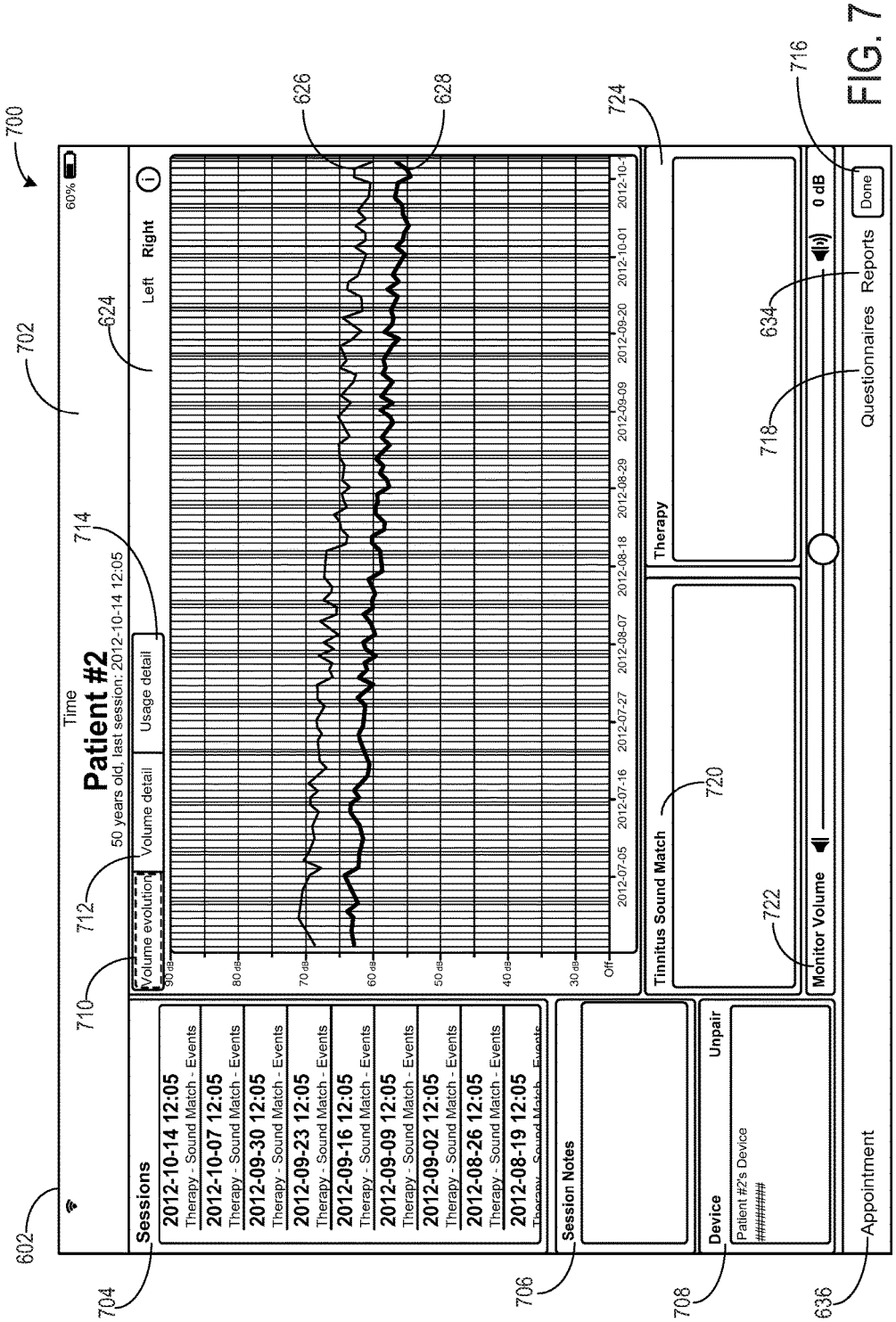
Figure 8:
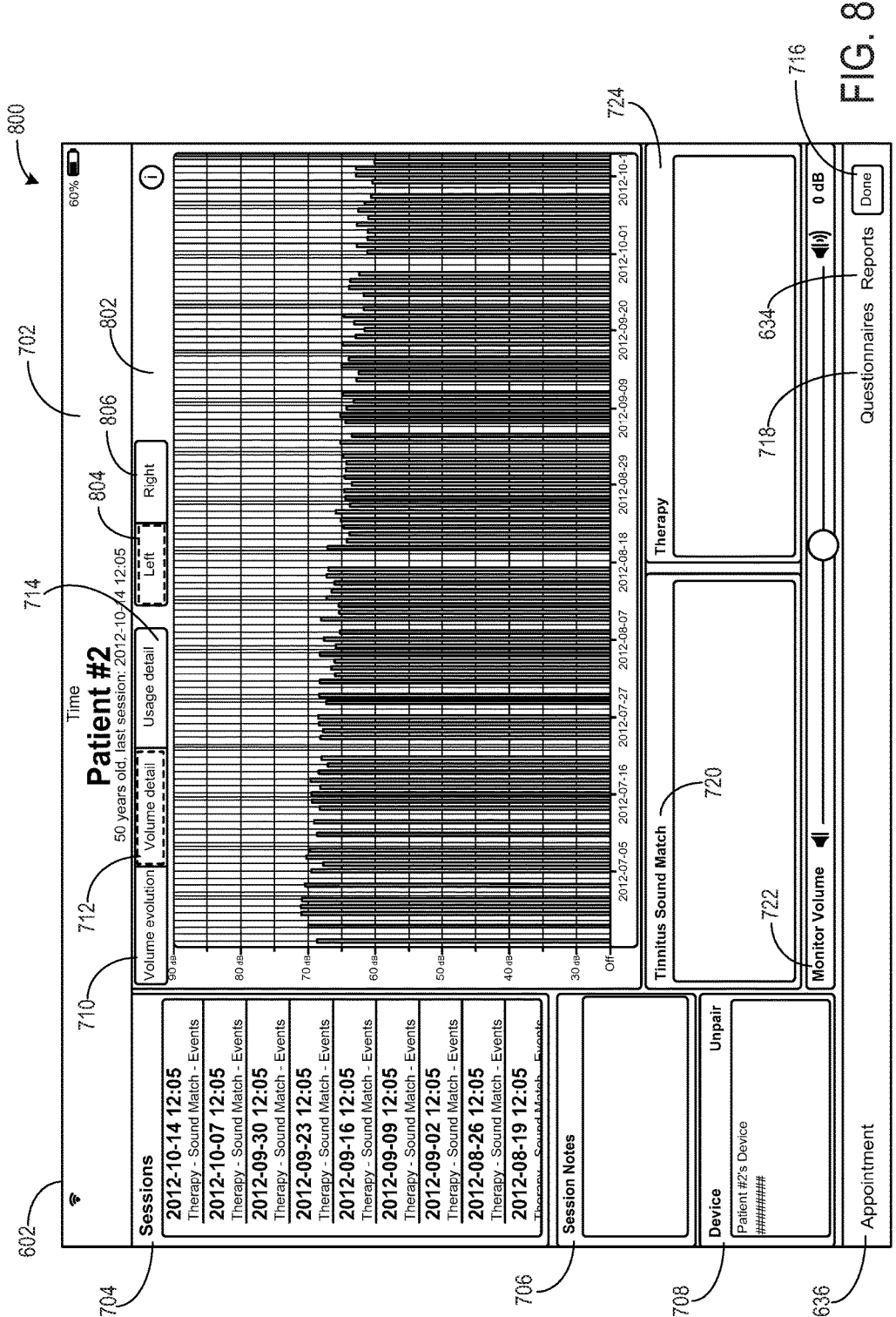
Figure 9:
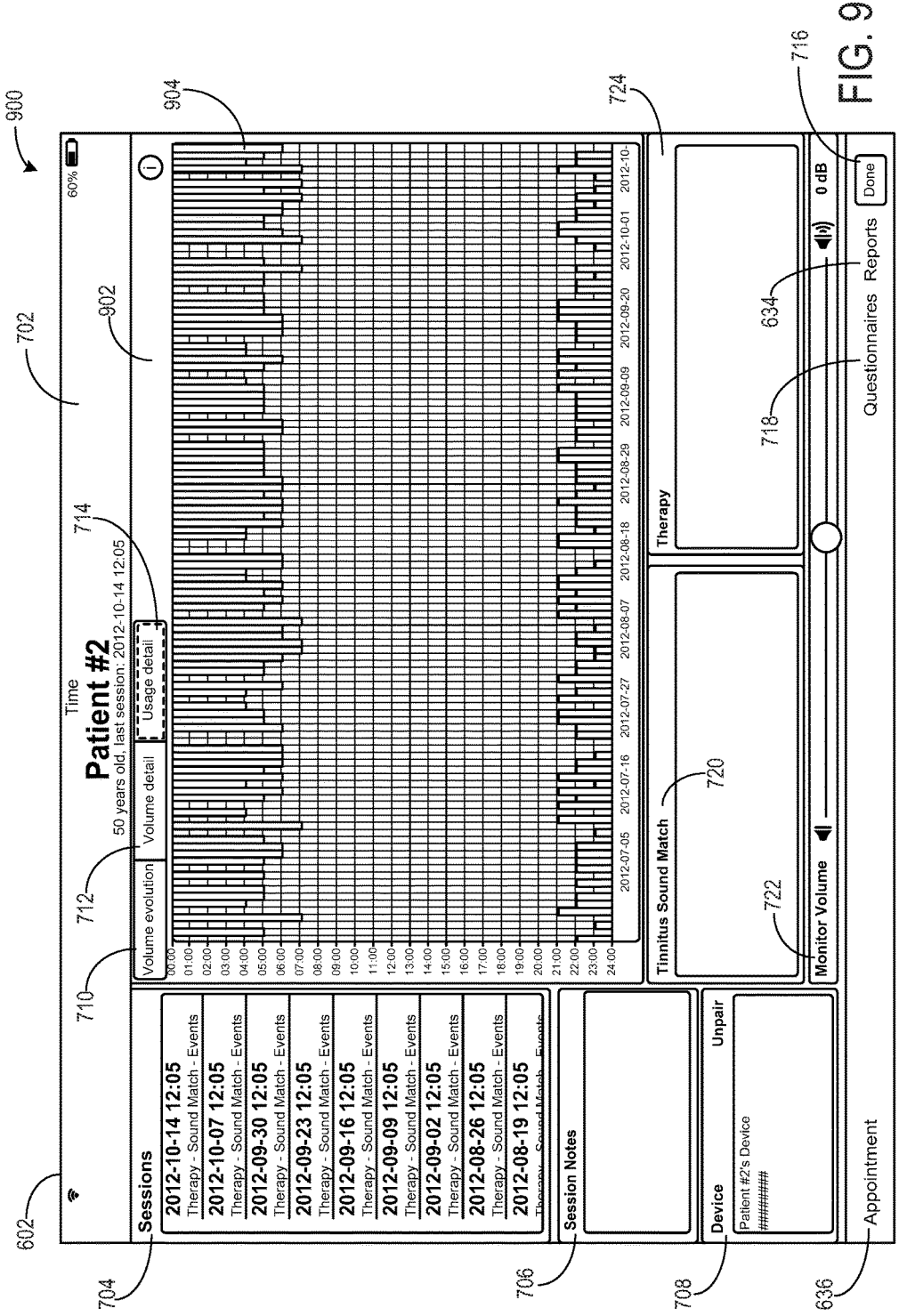
Figure 10:
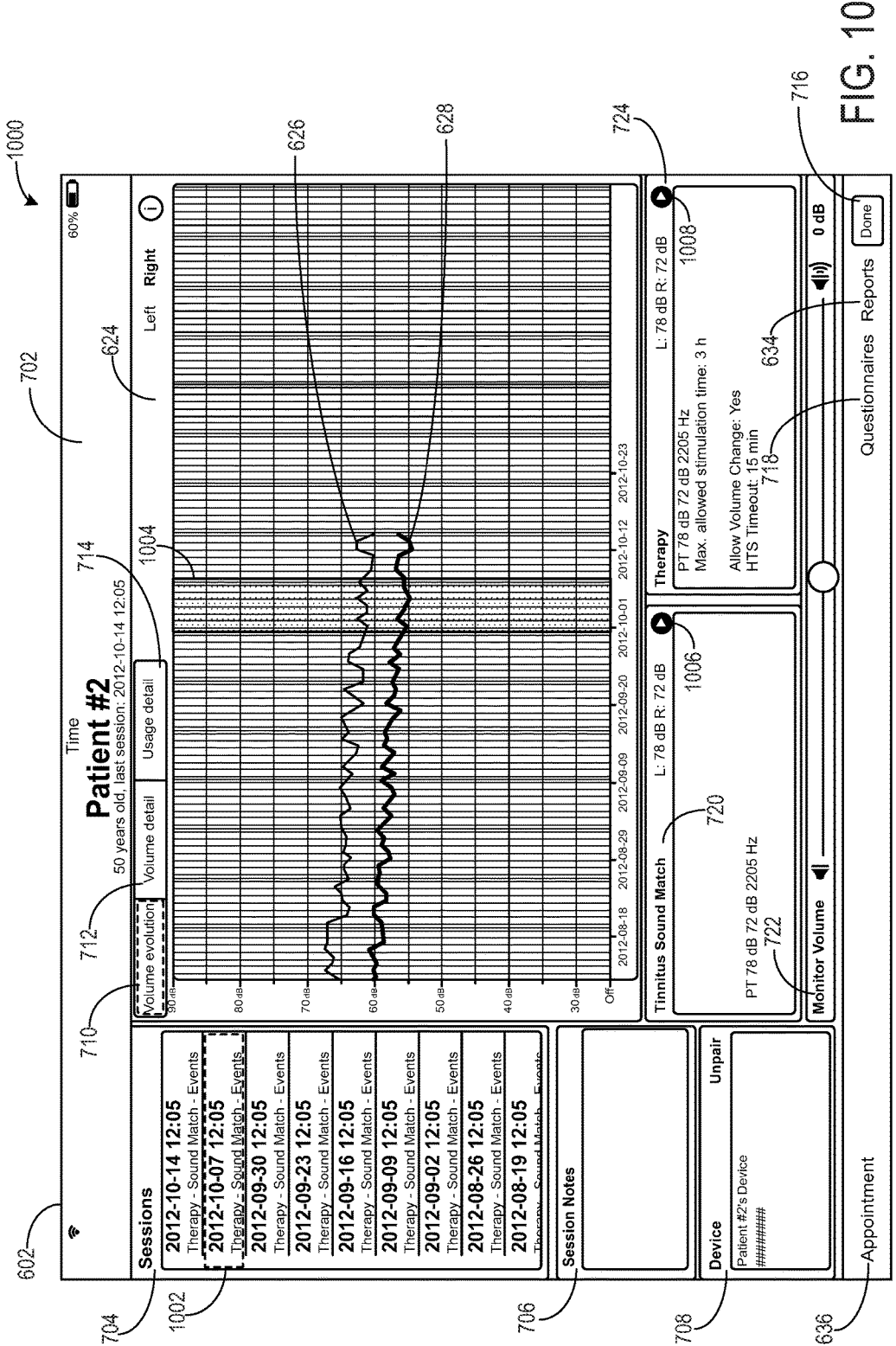
Figure 11:
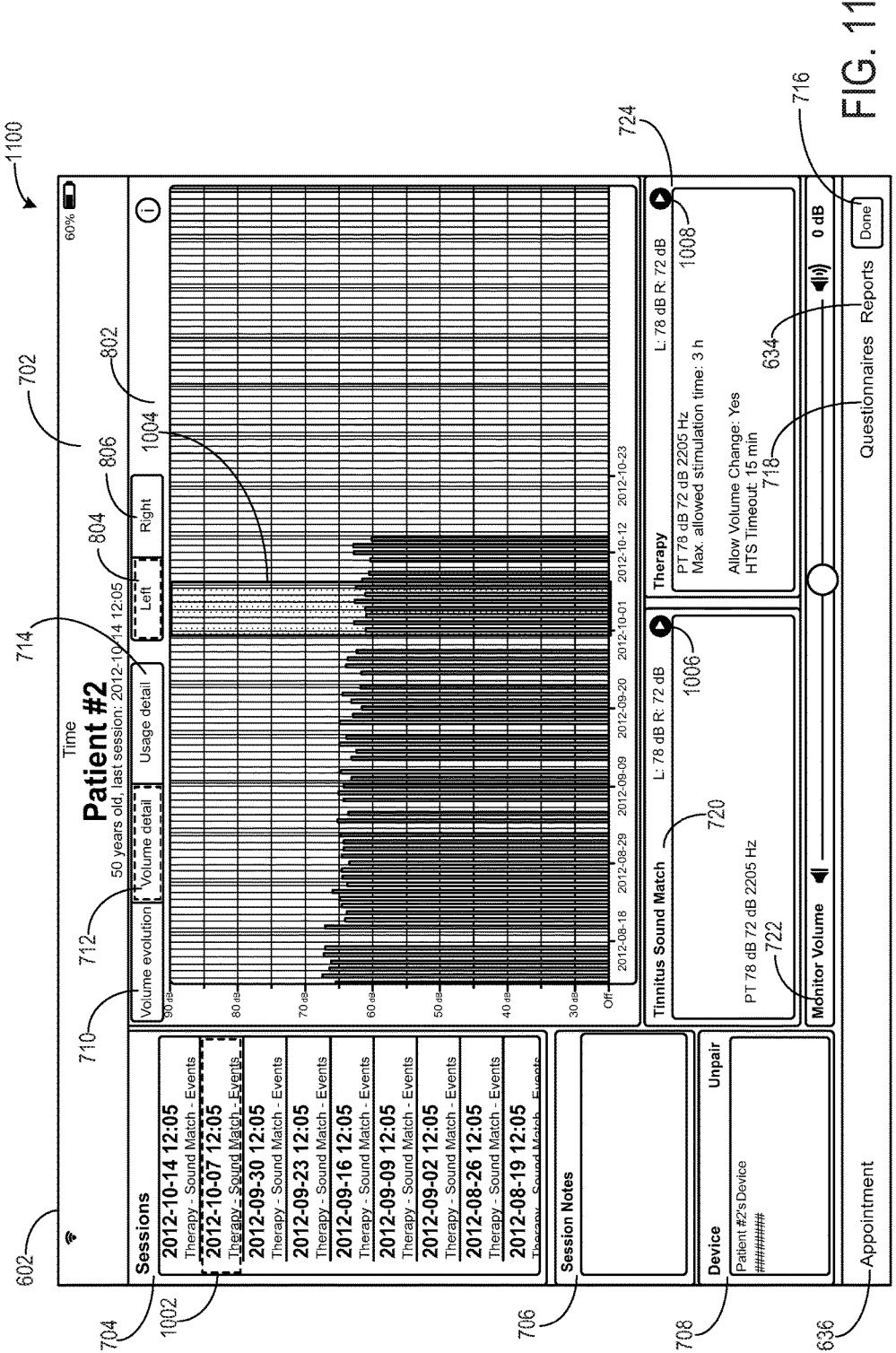
Figure 12:
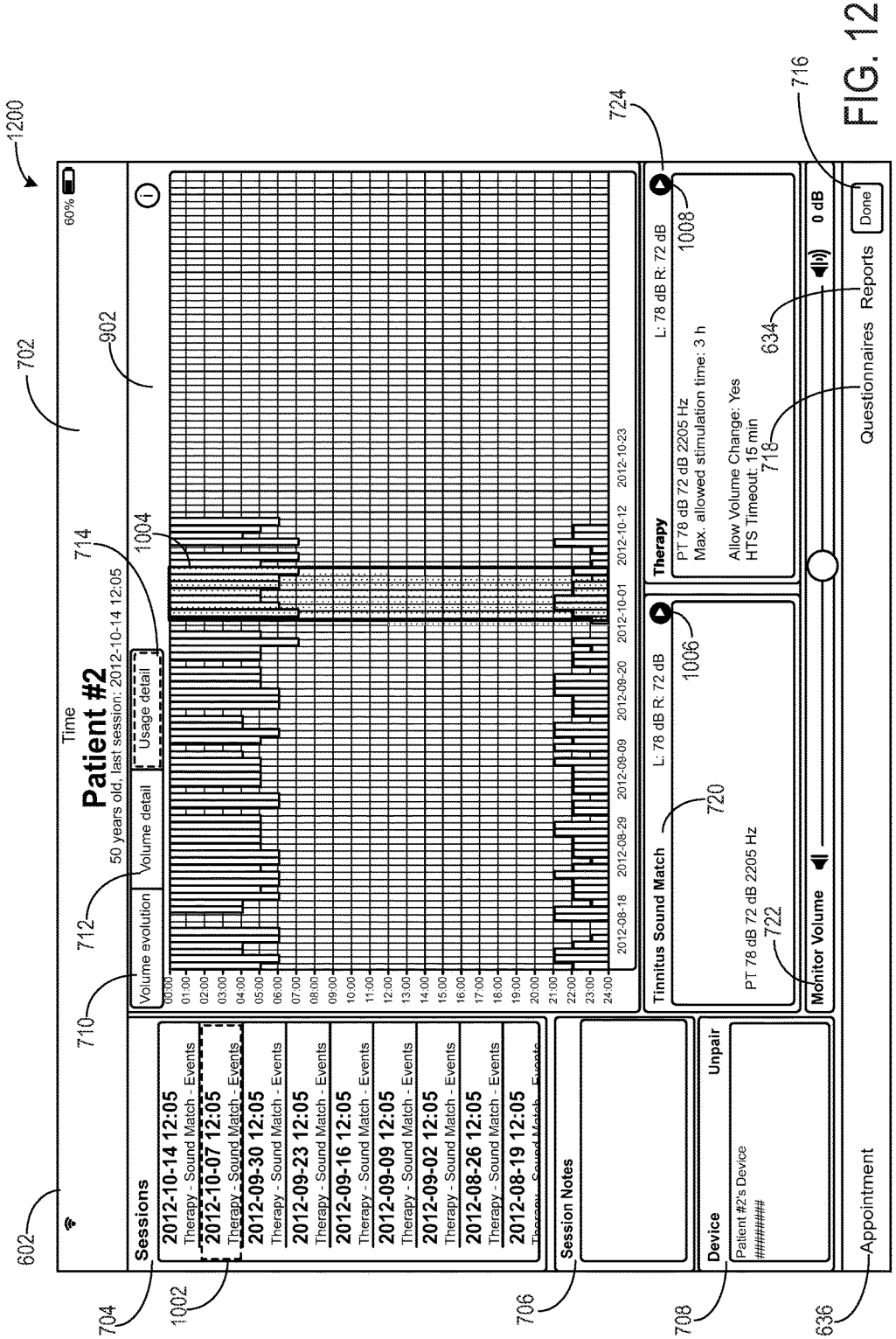

FIGS. 7-12 show schematics of the user interface 602 displaying a patient detail view screen 702. More specifically, FIG. 7 shows a schematic 700 of the patient detail view screen 702 displaying the volume evolution chart 624, FIG. 8 shows a schematic 800 of the patient detail view screen 702 displaying a volume detail chart 802, and FIG. 9 shows a schematic 900 of the patient detail view screen 702 displaying a usage detail chart 902. FIG. 10 shows a schematic 1000 of the patient detail view screen 702 displaying the volume evolution chart 624 with a selected session highlighted, FIG. 11 shows a schematic 1100 of the patient detail view screen 702 displaying a volume detail chart 802 with the selected session highlighted, and FIG. 12 shows a schematic 1200 of the patient detail view screen 702 displaying a usage detail chart 902 with the selected session highlighted.

The patient detail view screen 702 displays (e.g., presents) detailed information for a selected patient to a user, the detailed information providing a user a way to view and analyze tracked tinnitus therapy data including volume evolution and usage data. Specifically, the patient detail view screen 702 displays the selected patient's name, age, and date and time of the patient's last session (e.g., the last time that the patient listened to their tinnitus therapy sound). As shown in FIGS. 7-12, this information is displayed at a top of the patient detail view screen 702. At a bottom of the patient detail view screen 702, the appointment input 636, reports input 634, done button 716 and a questionnaires button 718 are displayed. The done button 716 may close the patient detail view screen 702 and return a user to the patient overview screen 605 shown in FIG. 6 and the questionnaires button may open a questionnaires screen for completing or conducting new questionnaires, as shown in FIG. 13, described further below.

The patient detail view screen 702 also includes a session list 704 displaying a list of all the patient's sessions. As such, the session list 704 reports a session history of the patient. The sessions may be labeled in the session list 704 with a date and time that the session occurred. The type of session may also be listed under each session in the session list 704 (e.g., therapy sound match event). When one of the sessions in the session list 704 is selected, a column corresponding to that session in the volume evolution chart may be highlighted, as shown in FIGS. 10-12, described further below.

A session notes box 706 may display any notes taken by the patient during the selected session. Additionally, a user may use the user interface 602 to add or edit notes to the session notes box 706. For example, a user may tap within the session notes box 706 and a keyboard may appear on the user interface 602 for entering notes into the session notes box 706. A device box 708 displays information specific to the selected patient's device (e.g., device name). The device box 708 may also allow a user to unpair the device from the selected patient.

Additionally, the patient detail view screen 702 includes a tinnitus sound match box 720 displaying the tinnitus sound match details. For example, when a session is highlighted, as shown in FIGS. 10-12, the tinnitus sound match box 720 may display the tinnitus sound match used during the selected session (e.g., shows an identifier or label corresponding to a specific tinnitus sound match). As discussed above, a user or patient may have more than one tinnitus sound match and use (e.g., listen to) different matches during different sessions. A user may listen to the tinnitus sound match used during the selected session by pressing a play button (shown in FIGS. 10-12). A user may also adjust the playback volume of the tinnitus sound match by adjusting a sliding monitor volume bar 722. A therapy box 724 displays tinnitus therapy details of a selected session (as shown in FIGS. 10-12). Tinnitus therapy details may include one or more of a help to sleep timeout (e.g., a duration of using the help to sleep option), allow volume change option, etc.

The patient detail view screen 702 includes a volume evolution button 710, a volume detail button 712, and a usage detail button 714. These three buttons allow a user to toggle between the volume evolution chart 624 (shown in FIG. 7 and FIG. 10, described further below), a volume detail chart (shown in FIG. 8 and FIG. 11, described further below), and a usage detail chart (shown in FIG. 9 and FIG. 12, described further below). When the volume evolution button 710 is selected, as shown in FIG. 7 and FIG. 10, the user interface 602 displays the volume evolution chart 624, as described with reference to FIG. 6 above.

When the volume detail button 712 is selected, as shown in FIG. 8 and FIG. 11, the user interface 602 displays the volume detail chart 802. The volume detail chart 802 shows a volume change (e.g., a volume change in dB) throughout a patient's therapy (e.g., over a series of therapy sessions). More specifically, the volume detail chart 802 shows volume on the y-axis and session date on the x-axis. A user may select either the left or right ear volume by selecting either the left ear button 804 or the right ear button 806, respectively. As such, only the left or right ear volume data may be displayed at one time on the volume detail chart 802. In other examples, both the left and right ear volume may be displayed at the same time on the volume detail chart 802. As shown in FIG. 8 and FIG. 11, the volume detail chart 802 is shown as a bar chart. In alternate embodiments, the volume detail chart 802 may be a line graph or other type of chart.

When the usage detail button 714 is selected, as shown in FIG. 9 and FIG. 12, the user interface 602 displays the usage detail chart 902. The usage detail chart 902 shows tracked data of when therapy sessions occurred. For example, the usage detail chart 902 shows time of day (e.g., 24-hour clock cycle) on the y-axis and date (e.g., session date) on the x-axis. Each bar 904 covers the hours that the tinnitus therapy was conducted (e.g., the hours that a patient listened to the tinnitus therapy sound) on each session date. The length of each bar may represent a duration of the therapy. Thus, longer bars represent a longer session duration. A user may see how consistently the patient uses the therapy.

As shown in FIGS. 10-12, when a specific therapy session is selected from the session list 704, the chart data corresponding to the selected session is highlighted on the selected chart (e.g., on the volume evolution chart 624, volume detail chart 802, or usage detail chart 902. For example, as shown in FIGS. 10-12, the second session 1002 is selected and thus that corresponding session is highlighted in the charts, as shown by box 1004. More specifically, the entire length of the data corresponding to the selected session is highlighted. As introduced above, the tinnitus sound match box 720 displays tinnitus sound match details and may include a play button 1006 for playing back the tinnitus sound match used during the selected session. In one example, the tinnitus sound match details may include an average volume for the left and right ear and/or a frequency of the sound match. Additionally, the therapy box 724 displays tinnitus therapy details of the selected session and may also include another play button 1008 for playing back the tinnitus sound match used during the selected session. The tinnitus therapy details may include one or more of a help to sleep timeout (e.g., a duration of using the help to sleep option), allow volume change option, etc. In one example, as shown above, only a single session may be selected and highlighted in the charts at once. In alternate embodiments, more than one session, or a series of sessions, may be selected and highlighted within the same chart.

Turning now to FIG. 13, user interface 602 is shown displaying a patient questionnaires screen 1302. As described above, the questionnaires screen 1302 may be displayed upon selecting the questionnaires button 718 on the patient detail view screen 702. The questionnaires screen 1302 may be used to display already completed questionnaires or create and conduct new questionnaires. Questionnaires may include hearing tests such as an audiogram hearing test (as shown in FIG. 4, described above) and/or tinnitus hearing-aid index (THI) tests. The questionnaires screen 1302 includes a display of the patient's name (e.g., Patient #2), the patient's age, and date of the patient's last therapy session. Any previously conducted questionnaires may be listed in the previous questionnaires list 1304. THI tests may be listed and/or data from THI tests may be listed in an additional list 1306 shown on the right-hand side of the questionnaires screen 1302. A new questionnaire may be created by selected the new questionnaire button 1308. For example, upon selecting the new questionnaire button 1308, an audiogram may be performed following the method outlined in FIG. 4.

Turning to FIGS. 14-15, an example evolution report 1400 is shown, the evolution report created from tracked tinnitus therapy data. As described in FIG. 5 above, one or more reports may be generated from tracked patient (e.g., therapy) data. FIG. 14 shows a first page of the evolution report 1400 displaying patient details and a volume evolution over a therapy duration (e.g., over a series of therapy sessions). The evolution report 1400 may include healthcare provider information, as shown at 1402, including a clinic name, address, healthcare provider name, and/or phone. The evolution report 1400 may further include patient personal information, as shown at 1404, including patient name, patient id (e.g., identifier information), patient gender, and/or patient birth date. At 1406, the evolution report 1400 may include a notes section where a user or healthcare provider may insert any notes pertaining to the patient, tinnitus therapy, and/or tracked data. At 1408, the evolution report 1400 may present statistics of the tinnitus therapy over the therapy duration (e.g., over the series of sessions included in the report). For example, as shown at 1408, the statistics section may include a date of the first session in the series of sessions, a date of the last session in the series of sessions, average daily use, average weekly use, and total number of sessions in the series of sessions. In alternate embodiments, the statistics section may include additional or alternative therapy statistics. Additionally, the usage data may be presented in different units (e.g., minutes per day vs. hours per day). At 1410, the evolution report 1400 includes a volume evolution chart. The volume evolution chart may be the same as the volume evolution chart 624 shown in FIG. 6, as described above. As such, the volume evolution chart displays changes in left ear and right ear volume (e.g., in dB or another volume measurement) over the series of sessions.

FIG. 15 shows an example second page of the evolution report 1400. The patient's name and/or patient ID may be displayed at a top of the second page (and any additional pages of the evolution report 1400). The second page of the evolution report 1400 displays details of each therapy session in the series of sessions. More specifically, the evolution report 1400 includes therapy details for each therapy session starting with the most recent. In alternate examples, the therapy sessions may be presented in an alternate order (e.g., oldest first). Each therapy session in the list includes a date of the therapy, a list of each sound component (e.g., each sound component of the tinnitus sound match), a frequency of each sound component, a volume for the left ear of each component, a volume for the right ear of each component, a total volume for the left and right ear, a maximum allowed stimulation time, whether an allow volume change was enabled, whether a help-to-sleep (HTS) option was enabled, and a duration of a HTS timeout.

For example, a first therapy session, labeled "Therapy 1", is shows at 1502. The sound type component of the tinnitus sound match (e.g., pure tone) and frequency of the sound component is shown at 1504. In this example, Patient #2's sound match only included a pure tone component at a frequency of 2205 Hz. Further, the left and right ear intensity of the sound match, as listened to by the user, is also listed at 1504. The additional therapy details, such as the maximum allowed stimulation time (e.g., duration of playing the sound match continuously without breaks), allow HTS, and allow volume change, is displayed at 1506. As shown at 1508, the left and right ear volume was decreased by the user during the therapy 4 session. The evolution report 1400 may include as many pages as necessary to present all the therapy sessions in the series of tracked therapy sessions.

As one example, a method for tinnitus therapy comprises tracking a tinnitus therapy over a duration, the tinnitus therapy including a tinnitus therapy sound matching a patient's perceived tinnitus played over the duration and presenting each of a volume evolution of the tinnitus therapy sound and usage data of the tinnitus therapy over the duration. Tracking the tinnitus therapy over the duration includes tracking volume changes to the tinnitus therapy sound. Further, in one example, tracking the tinnitus therapy over the duration includes tracking volume changes separately for a left ear input and a right ear input. In one example, the duration includes a series of sessions, the tinnitus therapy sound played continuously for a prescribed amount of time during each session of the series of sessions. Tracking the tinnitus therapy over the duration includes tracking one or more of a date, time, and duration of each session in the series of sessions. Additionally, the usage data includes one or more of a total number of sessions in the series of sessions, a date and time of a first session of the series of sessions, a date and time of a last session of the series of sessions, an average daily use, an average weekly use, and a length of each session. In one example, presenting the volume evolution of the tinnitus therapy sound includes visually presenting tracked changes to left and right ear volume inputs by a user over the duration in a volume evolution chart, the volume evolution chart including changes in volume vs. session date. The method may further comprise generating a report based on the tracked changes, the report including a volume evolution of the tinnitus therapy sound over the duration.

As another example, a method for tinnitus therapy comprises tracking changes to a tinnitus therapy over a duration, the tinnitus therapy including at least two different tinnitus sound matches based on a patient's perceived tinnitus, the tracking including individually tracking intensity changes to each of the at least two different sound matches. In one example, the individually tracking intensity changes to each of the at least two different sound matches includes individually tracking left and right ear input volume changes to each of the at least two different sound matches. The method may further comprise tracking usage of each of the at least two different tinnitus sound matches, wherein tracking usage includes tracking one or more of a date, time, and duration of each use of each of the at least two different tinnitus sound matches. As one example, a first match of the at least two different sound matches includes a different tinnitus sound type than a second match of the at least two different sound matches, the different tinnitus sound type including one of a pink noise, a cricket sound, a white noise, a broad band noise, or a pure tone sound. The method may further comprise displaying the individually tracked intensity changes together on a single chart.

As yet another example, a method for tinnitus therapy comprises tracking therapy data of a tinnitus therapy over time, the tinnitus therapy including a tinnitus sound matching a patient's perceived tinnitus, presenting the tracked therapy data, and adjusting the tinnitus therapy based on the tracked data. The method may further comprise presenting therapy details of the tinnitus therapy corresponding to the tracked therapy data, the therapy details including one or more of a list of each sound component of the tinnitus sound and a corresponding frequency level, a help-to-sleep option, an allow changing volume option, a prescribed therapy duration, and a prescribed time of day for therapy. Additionally, the method may further comprise playing back the tinnitus sound corresponding to the tracked therapy data. Adjusting the tinnitus therapy based on the tracked data includes adjusting one or more therapy parameters of the tinnitus therapy. The one or more therapy parameters may include sound parameters of one or more components of the tinnitus sound match, allow volume changes option, and/or the components (e.g., sound types) of the tinnitus sound match. Additionally, the tracked therapy data includes one or more of a volume evolution of the tinnitus sound over time, separate volume evolutions of the tinnitus sound over time for a right ear and left ear input and usage data, the usage data including one or more of a number of therapy sessions, an average daily usage, an average weekly usage, and a therapy duration for each session of the number of therapy sessions. In one example, tracking therapy data includes remotely tracking each of intensity changes to the tinnitus sound and usage of the tinnitus sound and remotely transferring tracked changes to a secured data network. In another example, the tracking therapy data includes tracking the therapy data with a first device, the first device used to deliver the tinnitus therapy and wherein presenting the tracked therapy data includes presenting the tracked data to a user via a user interface of a second device, the second device electronically coupled with the first device in order to transfer the tracked therapy data to the second device. The method may further comprise generating a patient medical record, the patient medical record including a patient audiogram, the tinnitus sound, the tracked therapy data and the adjusted tinnitus therapy.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for tinnitus therapy, comprising:
   presenting a plurality of different sound templates to a user from a series of tinnitus therapy sound templates, the series of tinnitus therapy sound templates including at least a noise spectrum, a pure tone, and a combined sound template;
   receiving a selection by the user of one or more of the plurality of different sound templates to generate a sound match;
   generating a tinnitus therapy including a tinnitus therapy sound based on the selections;
   applying the generated tinnitus therapy to a patient's ear with a sound generating device over a duration;
   displaying the generated sound match; and
   tracking the tinnitus therapy applied by the device over the duration, wherein displaying the generated sound match includes displaying a customized visual representation of an individual patient's therapy.

2. The method of claim 1, wherein tracking the tinnitus therapy over the duration includes tracking volume changes to the tinnitus therapy.

3. The method of claim 2, wherein the noise spectrum is a white noise.

4. The method of claim 2, wherein the noise spectrum is a pink noise.

5. The method of claim 2, wherein the noise spectrum is band noise.

6. The method of claim 2, wherein the noise spectrum is broad-band noise.

7. The method of claim 1, wherein the series of tinnitus therapy sound templates include a cricket sound.

8. The method of claim 1, wherein the series of tinnitus therapy sound templates include an amplitude modulate sine wave.

9. The method of claim 1, wherein the duration includes a series of sessions, the tinnitus therapy sound played continuously for a prescribed amount of time during each session of the series of sessions.

10. The method of claim 9, wherein tracking the tinnitus therapy over the duration includes tracking one or more of a date, time, and duration of each session in the series of sessions.

11. The method of claim 8, further comprising presenting usage data of the tinnitus therapy over the duration.

12. The method of claim 11, wherein the usage data includes a total number of sessions in a series of sessions.

13. The method of claim 11, wherein the usage data includes a date and time of a first session of a series of sessions.

14. The method of claim 11, wherein the usage data includes, a date and time of a last session of a series of sessions.

15. The method of claim 11, wherein the usage data includes, an average use.

16. The method of claim 11, wherein the usage data includes, a length of a session.

17. The method of claim 1, further comprising presenting a volume evolution of the tinnitus therapy sound over the duration, wherein presenting the volume evolution of the tinnitus therapy sound includes visually presenting tracked changes to left and right ear volume inputs by the user over the duration.

18. A method for tinnitus therapy, comprising:
    presenting each of a noise, a pure tone, and a combined tone tinnitus therapy sound template to a user;
    generating a tinnitus therapy sound based on one or more tinnitus therapy sound templates selected by the user;
    adjusting the tinnitus therapy sound based on at least one of a frequency parameter and an intensity parameter selected by the user;
    applying the adjusted tinnitus therapy sound to a patient's ear with a sound generating device over a duration; and
    tracking at least one parameter change of the tinnitus therapy sound applied over the duration and communicating the tracked changes, including displaying a customized visual representation of an individual patient's therapy on a graphical user interface.

19. The method of claim 18, further comprising generating a report based on the tracked parameter change.

20. The method of claim 19, further comprising tracking usage of the applied adjusted tinnitus therapy sound, wherein tracking usage includes tracking one or more of a date, time, and duration of the applied adjusted tinnitus therapy sound.

* * * * *